(12) United States Patent
Kubota et al.

(10) Patent No.: US 10,139,319 B2
(45) Date of Patent: Nov. 27, 2018

(54) SAMPLE SMEARING APPARATUS

(71) Applicant: SYSMEX CORPORATION, Kobe-shi, Hyogo (JP)

(72) Inventors: Shogo Kubota, Kobe (JP); Mitsuo Yamasaki, Kobe (JP); Seiya Shinabe, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 2 days.

(21) Appl. No.: 15/498,529

(22) Filed: Apr. 27, 2017

(65) Prior Publication Data

US 2017/0315029 A1 Nov. 2, 2017

(30) Foreign Application Priority Data

Apr. 28, 2016 (JP) ................................ 2016-092067
Aug. 31, 2016 (JP) ................................ 2016-169110

(51) Int. Cl.
| | | |
|---|---|---|
| *G01N 1/00* | (2006.01) | |
| *G01N 1/28* | (2006.01) | |
| *G01N 35/00* | (2006.01) | |
| *G01N 35/04* | (2006.01) | |

(52) U.S. Cl.
CPC ..... *G01N 1/2813* (2013.01); *G01N 35/00029* (2013.01); *G01N 35/04* (2013.01); *G01N 2001/2826* (2013.01); *G01N 2035/00039* (2013.01); *G01N 2035/00138* (2013.01)

(58) Field of Classification Search
CPC ...................................................... G01N 1/00
See application file for complete search history.

(56) References Cited

U.S. PATENT DOCUMENTS

| | | | | |
|---|---|---|---|---|
| 5,209,903 | A | * 5/1993 | Kanamori | ............ G01N 1/2813 |
| | | | | 422/44 |
| 5,270,012 | A | 12/1993 | Kanamori et al. | |
| 2009/0155841 | A1 | 6/2009 | Yamasaki | |
| 2009/0223390 | A1 | 9/2009 | Schlinkmann et al. | |

FOREIGN PATENT DOCUMENTS

| | | |
|---|---|---|
| CN | 203877403 U | 10/2014 |
| CN | 203877556 U | 10/2014 |
| JP | H04-21951 A | 1/1992 |
| JP | H08-271390 A | 10/1996 |
| JP | 2000-074803 A | 3/2000 |
| JP | 2005-315754 A | 11/2005 |
| JP | 2009-145261 A | 7/2009 |
| WO | 2015165019 A1 | 11/2015 |

* cited by examiner

*Primary Examiner* — Jyoti Nagpaul
(74) *Attorney, Agent, or Firm* — Metrolexis Law Group, PLLC

(57) ABSTRACT

A sample smearing apparatus of an embodiment includes: a first slide glass feeder that feeds a slide glass before processing; a slide glass transporter including a slide glass holder that holds the slide glass, that is capable of receiving the slide glass at a first slide glass feeding position from the first slide glass feeder, and transports the received slide glass while holding the slide glass with the slide glass holder; and a slide processor that performs processing on the slide glass held by the slide glass holder.

20 Claims, 13 Drawing Sheets

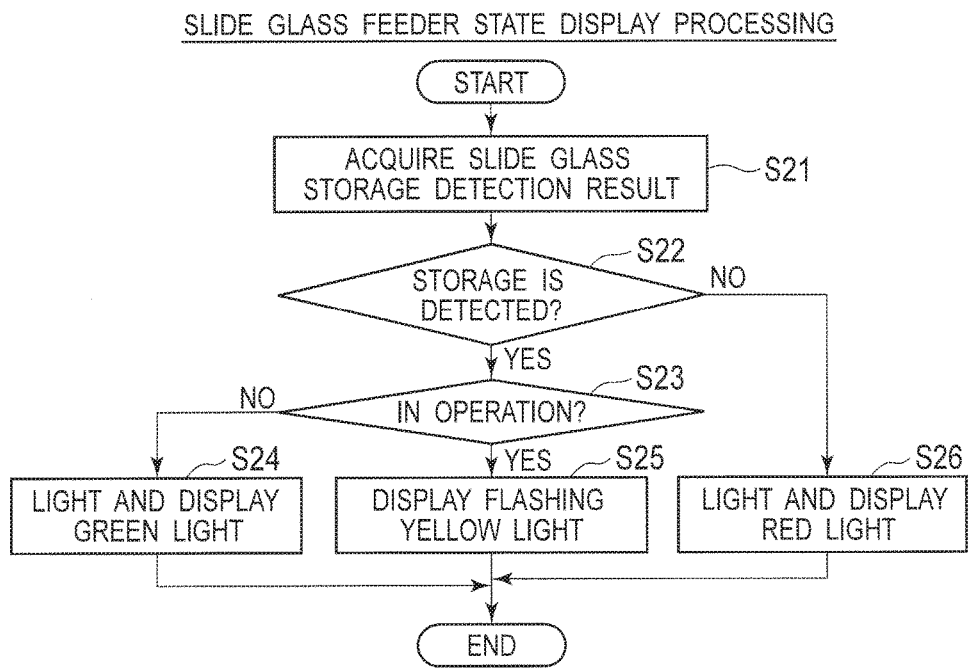
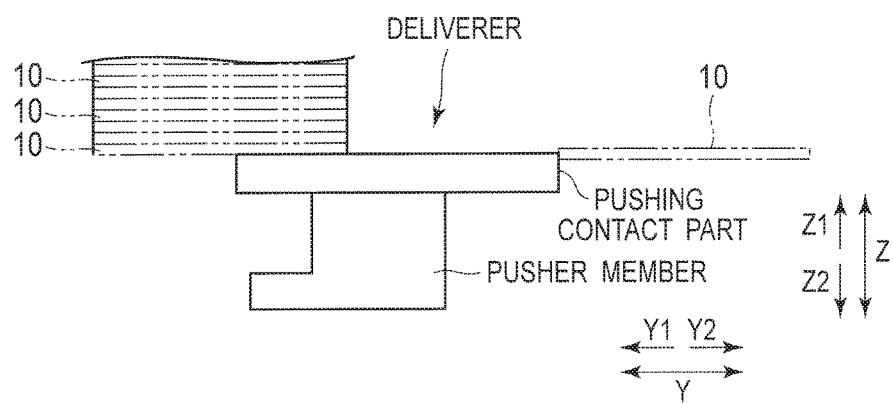

SAMPLE SMEARING APPARATUS

CROSS REFERENCE TO RELATED APPLICATIONS

This application claims priority based on 35 USC 119 from prior Japanese Patent Applications Nos. 2016-092067 filed on Apr. 28, 2016, and 2016-169110 filed on Aug. 31, 2016, entitled "SAMPLE SMEARING APPARATUS", the entire contents of which are incorporated herein by reference.

BACKGROUND

The disclosure relates to a sample smearing apparatus.

Japanese Patent Application Publication No. 2009-145261 (Patent Literature 1) discloses a sample smearing apparatus including: a slide glass feeder which feeds a slide glass; a first slide transporter and a second slide transporter, which transport the slide glass; and a processor which performs processing for smearing a sample on the slide glass. The slide glass feeder feeds the slide glass to a feeding position in the first slide transporter. Also, the first slide transporter transports the slide glass and passes the slide glass to the second slide transporter. The second slide transporter transports the received slide glass to the processor.

In the Patent Literature 1, the slide glass is fed to the first slide transporter from the slide glass feeder, and the slide glass is transported by the first slide transporter and passed to the second slide transporter. Thereafter, the slide glass is transported to the processor by the second slide transporter.

As described above, in the conventional sample smearing apparatus, the first slide transporter for transporting the slide glass fed by the slide glass feeder to the second slide transporter is provided separately from the second slide transporter for transporting the received slide glass to the processor. As a result, the apparatus configuration becomes complicated, and the sample smearing apparatus is increased in size.

SUMMARY

One or more embodiments of sample smearing apparatus may include: a first slide glass feeder that feeds a slide glass before processing; a slide glass transporter including a slide glass holder that holds the slide glass, that is capable of receiving the slide glass at a first slide glass feeding position from the first slide glass feeder, and transports the received slide glass while holding the slide glass with the slide glass holder; and a slide processor that performs processing on the slide glass held by the slide glass holder.

One or more embodiments of sample smearing apparatus may include: a slide glass feeder that holds slide glasses in a stacked state; and a deliverer that delivers the slide glasses from the slide glass feeder, wherein the deliverer includes a pusher member that protrudes upward from a lower surface of the lowest slide glass among the stacked slide glasses, and pushes the slide glass in a predetermined direction, and the pusher member includes a pushing contact part that is provided on one side of the pusher member in the predetermined direction and that comes into contact with the slide glass, and an inclined part that is provided at an upper end on the opposite side of the pusher member in the predetermined direction, and which is inclined downward while extending in the opposite direction from the predetermined direction.

BRIEF DESCRIPTION OF DRAWINGS

FIG. 22 is a flowchart illustrating slide glass feed state display processing.

FIG. 23 is a side view illustrating a deliverer in a sample smearing apparatus according to a modified example of the embodiment.

DETAILED DESCRIPTION

Figure 1:
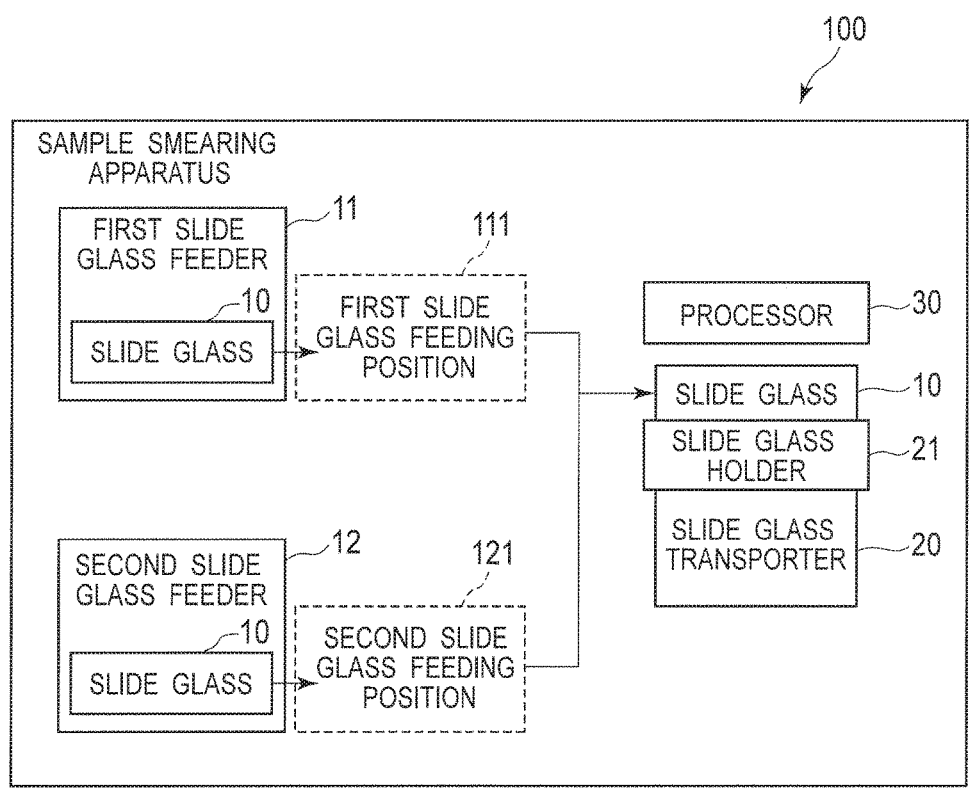
FIG. 1 is a schematic view illustrating an overview of a sample smearing apparatus according to one or more embodiments.

Embodiments are explained with reference to drawings. In the respective drawings referenced herein, the same constituents are designated by the same reference numerals and duplicate explanation concerning the same constituents is basically omitted. All of the drawings are provided to illustrate the respective examples only. No dimensional proportions in the drawings shall impose a restriction on one or more embodiments. For this reason, specific dimensions and the like should be interpreted with the following descriptions taken into consideration. In addition, the drawings may include parts whose dimensional relationship and ratios are different from one drawing to another.

[Overview of Sample Smearing Apparatus]

With reference to FIG. 1, description is given of an overview of sample smearing apparatus 100 according to this embodiment.

Sample smearing apparatus 100 is an apparatus for smearing a sample on slide glass 10. The sample is a biological sample collected from a sample under test (subject), for example, blood, cells, and the like.

As illustrated in FIG. 1, sample smearing apparatus 100 includes first slide glass feeder 11. Sample smearing apparatus 100 also includes slide glass transporter 20 and slide processor 30. Slide glass transporter 20 includes slide glass holder 21 that holds slide glass 10. Sample smearing apparatus 100 may also include second slide glass feeder 12. In the configuration example illustrated in FIG. 1, sample smearing apparatus 100 includes first slide glass feeder 11 and second slide glass feeder 12. Note that holding by slide glass holder 21 means that slide glass 10 is set in a fixed state so that slide glass 10 does not move. For example, a holding method includes gripping by sandwiching the slide glass to be fixed. Also, a method of imparting the gripping force is not limited to elastic force of a spring, but also includes other elastic force, gravity, fluid pressure, and the like, for example. Meanwhile, the holding method includes fixing by adsorption. Alternatively, the slide glass may be held by another method.

Slide glass 10 is a rectangular plate-like member, for example. Slide glass 10 has, for example, a smear region for smearing the sample and a print region for displaying various kinds of information such as sample information. The smear region is formed in a predetermined range extending in a longitudinal direction in the center of slide glass 10 in the longitudinal direction, for example. The print region is formed away from the smear region at one end of slide glass 10 in the longitudinal direction. The print region is a part that is processed to be printable by coating slide glass 10 with a resin material or the like, for example. In the print region, a sample number, a date, a bar code or two-dimensional code, and the like can be printed.

First slide glass feeder 11 feeds slide glasses 10 before smearing (before processing) one by one. First slide glass feeder 11 can also house more than one slide glass 10. First slide glass feeder 11 passes slide glass 10 to slide glass transporter 20 at first slide glass feeding position 111. First slide glass feeding position 111 is located adjacent to first slide glass feeder 11.

Second slide glass feeder 12 feeds slide glasses 10 before smearing (before processing) one by one. Second slide glass feeder 12 can also house more than one slide glass 10. Second slide glass feeder 12 passes slide glass 10 to slide glass transporter 20 at second slide glass feeding position 121. Second slide glass feeding position 121 is a position different from first slide glass feeding position 111.

Slide glass transporter 20 can be moved to first slide glass feeding position 111. Slide glass transporter 20 can also move to second slide glass feeding position 121. Moreover, slide glass transporter 20 receives one slide glass 10 from first slide glass feeder 11 or second slide glass feeder 12. More specifically, slide glass transporter 20 can receive slide glass 10 at first slide glass feeding position 111 from first slide glass feeder 11. Likewise, slide glass transporter 20 can receive slide glass 10 at second slide glass feeding position 121 from second slide glass feeder 12. Also, slide glass transporter 20 transports slide glass 10 thus received. To be more specific, slide glass transporter 20 transports received slide glass 10 while holding the slide glass on an upper surface thereof. Moreover, slide glass transporter 20 uses slide glass holder 21 to hold slide glass 10. Furthermore, slide glass transporter 20 transports held slide glass 10 to slide processor 30.

Slide processor 30 performs processing on slide glass 10. To be more specific, slide processor 30 performs processing for smearing the sample on slide glass 10 held by slide glass holder 21 in slide glass transporter 20. Slide processor 30 performs at least one of processing of smearing the sample on slide glass 10, processing of printing information on slide glass 10, and processing of removing extraneous matter adhering to slide glass 10, for example.

With the above configuration, in sample smearing apparatus 100, receiving slide glass 10 fed by first slide glass feeder 11 or second slide glass feeder 12 and transporting slide glass 10 to slide processor 30 can be both performed by common slide glass transporter 20. Thus, an increase in the number of the slide glass transporters can be suppressed. As a result, the apparatus configuration of sample smearing apparatus 100 can be simplified. Also, as much as the number of the slide glass transporters can be reduced, sample smearing apparatus 100 can be reduced in size. Moreover, since the number of times of passing slide glasses 10 can be reduced, the number of mechanisms for passing slide glasses 10 can be reduced. Furthermore, first slide glass feeding position 111 where first slide glass feeder 11 passes slide glass 10 to slide glass transporter 20 and second slide glass feeding position 121 where second slide glass feeder 12 passes slide glass 10 to slide glass transporter 20 are located at different positions. This eliminates the need for providing a space for disposing slide glass transporter 20 between first slide glass feeder 11 and second slide glass feeder 12. Moreover, slide processor 30 can perform processing on slide glass 10 in a held state by slide glass transporter 20. This also eliminates the need for additionally providing a transfer mechanism for transferring slide glass 10 during the processing by slide processor 30. Furthermore, in a case of two-dimensionally transferring slide glass 10, when more than one transporter is provided, every change in transfer direction requires the transporter. On the other hand, common slide glass transporter 20 can two-dimensionally transport slide glass 10. As a result, the apparatus configuration can be simplified, and thus sample smearing apparatus 100 can be reduced in size.

[Configuration Example of Smear Preparation Apparatus]

Figure 2:
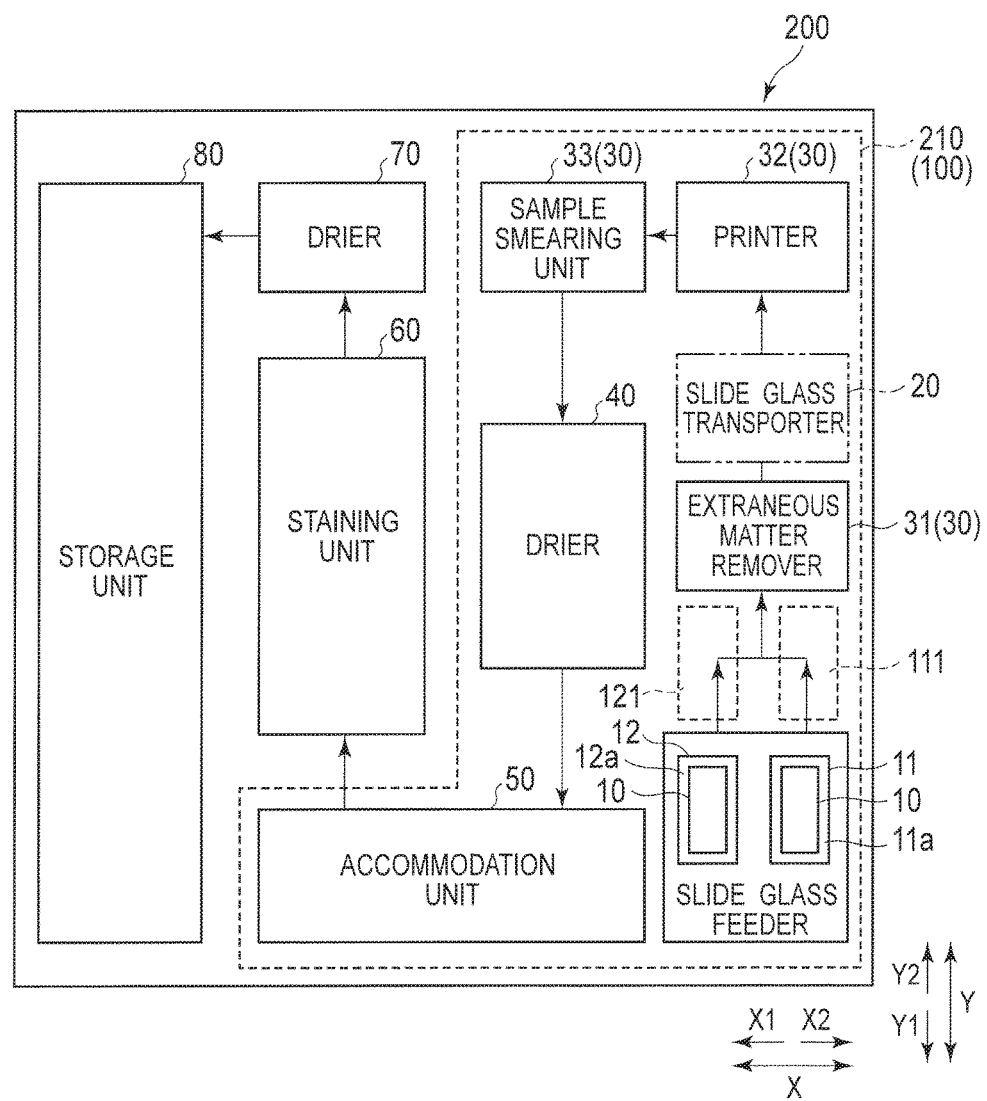
FIG. 2 is a schematic plan view for explaining an example of an overall configuration of a smear preparation apparatus.

With reference to FIG. 2, description is given below of a configuration example of smear preparation apparatus 200, in which sample smearing apparatus 100 illustrated in FIG. 1 is applied to a sample smearing unit in smear preparation apparatus 200. Smear preparation apparatus 200 is an apparatus for performing smearing processing of smearing a sample on slide glass 10 and also performing sample staining processing on slide glass 10 with the sample smeared thereon. The sample is blood, for example.

(Overall Configuration)

With reference to FIG. 2, an overall configuration of smear preparation apparatus 200 is described.

In the configuration example of FIG. 2, sample smearing apparatus 100 including first slide glass feeder 11, second slide glass feeder 12, slide glass transporter 20, and slide processor 30 illustrated in FIG. 1 is provided in smearing unit 210 in smear preparation apparatus 200. In the configuration example of FIG. 2, smearing unit 210 includes first slide glass feeder 11, second slide glass feeder 12, slide glass transporter 20, slide processor 30, drier 40, and accommodation unit 50. Slide processor 30 includes extraneous matter remover 31, printer 32, and sample smearing unit 33. Also, in the configuration example of FIG. 2, smear preparation apparatus 200 further includes staining unit 60, drier 70, and storage unit 80. Note that, in the following description, it is assumed that a short-side direction of slide glass 10 in first slide glass feeder 11 or second slide glass feeder 12 is an X-direction and a long-side direction thereof is a Y-direction. It is also assumed that a vertical direction is a Z-direction. In other words, slide glasses 10 are housed flat with their smearing surfaces horizontally set in first slide glass feeder 11 and second slide glass feeder 12. Moreover, first slide glass feeder 11 and second slide glass feeder 12 hold slide glasses 10 in a state where the X-direction of smear preparation apparatus 200 corresponds to the short-side direction of slide glass 10 and the Y-direction of smear preparation apparatus 200 corresponds to the long-side direction of slide glass 10.

First slide glass feeder 11 houses a number of slide glasses 10 in an unused state before smearing of the sample. To be more specific, first slide glass feeder 11 includes first case part 11a for holding slide glasses 10 before processing in a stacked state. In other words, first slide glass feeder 11 can hold slide glasses 10 in a vertically stacked state. First slide glass feeder 11 can feed slide glasses 10 before smearing to slide glass transporter 20 one by one at first slide glass feeding position 111. Slide glass 10 has a rectangular shape.

Second slide glass feeder 12 houses a number of slide glasses 10 in an unused state before smearing of the sample. To be more specific, second slide glass feeder 12 includes second case part 12a for holding slide glasses 10 before processing in a stacked state. In other words, second slide glass feeder 12 can hold slide glasses 10 in a vertically stacked state. Second slide glass feeder 12 can feed slide glasses 10 before smearing to slide glass transporter 20 one by one at second slide glass feeding position 121. Note that three or more slide glass feeders may be provided.

Slide glasses 10 housed in first slide glass feeder 11 and slide glasses 10 housed in second slide glass feeder 12 may be those of the same kind. In this case, when a number of slide glasses 10 of the same kind are to be used, slide glasses 10 are fed by two slide glass feeders (first slide glass feeder 11 and second slide glass feeder 12). Thus, workload of replenishing slide glasses 10 can be reduced.
Alternatively, slide glasses 10 housed in first slide glass feeder 11 and slide glasses 10 housed in second slide glass feeder 12 may be those of different kinds. In this case, smears can be prepared by using different kinds of slide glasses 10. The different kinds of slide glasses are those with print regions colored in different colors (for example, white, yellow, blue, and the like).

First slide glass feeder 11 and second slide glass feeder 12 are arranged side by side in the short-side direction of slide glasses 10 housed therein. More specifically, first and second slide glass feeders 11 and 12 are arranged side by side in the X-direction. First slide glass feeder 11 is disposed on the X2-direction side of second slide glass feeder 12. Thus, the shape of an area where first and second slide glass feeders 11 and 12 are disposed can be suppressed from being elongated, compared with a case where first and second slide glass feeders 11 and 12 are arranged in the long-side direction of slide glasses 10. As a result, smear preparation apparatus 200 can be suppressed from getting increased in length in the Y-direction (depth direction).

First slide glass feeding position 111 is located at one side of first slide glass feeder 11 in the long-side direction of slide glass 10. In the configuration example illustrated in FIG. 2, first slide glass feeding position 111 is located on the Y2-direction side of first slide glass feeder 11, which is the back direction side of smear preparation apparatus 200.

More specifically, first slide glass feeder 11 is disposed on the front side (Y1-direction side) of smear preparation apparatus 200. Also, slide glasses 10 are fed from the front side to the back side of smear preparation apparatus 200. Therefore, first slide glass feeder 11 is disposed in the front part of smear preparation apparatus 200. This can facilitate operations to be performed on first slide glass feeder 11. Such operations on first slide glass feeder 11 include, for example, operations of replenishing and replacing slide glasses 10, and the like.

Second slide glass feeding position 121 is located at one side of second slide glass feeder 12 in the long-side direction of slide glass 10. In the configuration example illustrated in FIG. 2, second slide glass feeding position 121 is located on the Y2-direction side of second slide glass feeder 12, which is the back direction side of smear preparation apparatus 200. More specifically, second slide glass feeder 12 is disposed on the front side (Y1-direction side) of smear preparation apparatus 200. Also, slide glasses 10 are fed from the front side to the back side of smear preparation apparatus 200. Therefore, second slide glass feeder 12 is disposed in the front part of smear preparation apparatus 200. This can facilitate operations to be performed on second slide glass feeder 12. Such operations on second slide glass feeder 12 include, for example, operations of replenishing and replacing slide glasses 10, and the like.

Slide glass transporter 20 can transport slide glasses 10 while holding slide glasses 10 on its upper surface. To be more specific, slide glass transporter 20 can transport held slide glasses 10 to extraneous matter remover 31, printer 32, and sample smearing unit 33. Moreover, in each of extraneous matter remover 31, printer 32, and sample smearing unit 33, slide glasses 10 held by slide glass transporter 20 are subjected to processing for smearing the sample in a state of being held by slide glass transporter 20.

Slide glass transporter 20 can receive slide glass 10 from first slide glass feeder 11 at first slide glass feeding position 111. Slide glass transporter 20 can also receive slide glass 10 from second slide glass feeder 12 at second slide glass feeding position 121. Moreover, slide glass transporter 20 can be moved in the horizontal direction (XY-direction). Furthermore, slide glass transporter 20 can transfer held slide glass 10 in the vertical direction (Z-direction).

Slide glass transporter 20 transports received slide glass 10 to extraneous matter remover 31, printer 32, and sample smearing unit 33 in this order. In sample smearing unit 33, slide glass 10 is passed to drier 40 from slide glass transporter 20. More specifically, slide glass transporter 20 transports held slide glass 10 to extraneous matter remover 31. Then, slide glass transporter 20 transports held slide glass 10 to printer 32 after extraneous matter is removed by extraneous matter remover 31. Thereafter, slide glass transporter 20 transports held slide glass 10 to sample smearing unit 33 after printing is performed by printer 32. Subsequently, slide glass transporter 20 passes slide glass 10 to drier 40 after smearing of the sample is performed by sample smearing unit 33.

Extraneous matter remover 31 is provided to remove extraneous matter adhering to the surface of slide glass 10. Also, extraneous matter remover 31 performs extraneous matter removal processing on slide glass 10 held on the upper surface of slide glass transporter 20. For example, extraneous matter remover 31 is connected to an unillustrated pressure source, and can blow off extraneous matter in the smear region and the print region on slide glass 10 by discharging air. The extraneous matter is, for example, small foreign matter such as glass powder and dust. Extraneous matter remover 31 removes the extraneous matter on the upper surface of slide glass 10 by discharging air in a state where slide glass transporter 20 holding slide glass 10 is lowered (see FIG. 10). Information can be clearly printed in the print region on slide glass 10 by extraneous matter remover 31 removing the extraneous matter on slide glass 10. Moreover, foreign matter can be prevented from being mixed into the sample during smearing of the sample on slide glass 10. In the configuration example of FIG. 2, extraneous matter remover 31 is disposed on the Y2-direction side of first and second slide glass feeders 11 and 12.

Printer 32 prints various kinds of information such as sample information in the print region on slide glass 10. Also, printer 32 performs printing on slide glass 10 held on the upper surface of slide glass transporter 20. Printer 32 uses a print head included therein to perform print processing from above slide glass 10 in a state where slide glass transporter 20 holding slide glass 10 is lifted (see FIG. 11). Printer 32 includes a heretofore known print head such as those of a thermal-transfer printer and an ink-jet printer. In the configuration example of FIG. 2, printer 32 is disposed on the Y2-direction side of extraneous matter remover 31.

Sample smearing unit 33 can smear the sample on slide glass 10. To be more specific, sample smearing unit 33 performs smearing of the sample on slide glass 10 held on the upper surface of slide glass transporter 20. The smearing processing by sample smearing unit 33 is processing of smearing the sample in the smear region on the surface of slide glass 10. For the smearing processing, a smearing method (so-called wedge method) using a smearing member such as a drawing glass, or other smearing methods can be adopted. Sample smearing unit 33 performs the smearing processing by using a smearing mechanism corresponding to the smearing method to be adopted. Moreover, sample smearing unit 33 can smear the sample by aspirating the sample with an unillustrated sample aspiration mechanism and dropping the sample in the smear region on slide glass 10. Sample smearing unit 33 performs the sample smearing processing in a state where slide glass transporter 20 is lifted until slide glass 10 comes into contact with a vertical positioning member in sample smearing unit 22 (see FIG. 12). In the configuration example of FIG. 2, sample smearing unit 33 is disposed on the X1-direction side of printer 32.

Drier 40 has a function to receive slide glass 10 with the sample smeared thereon from slide glass transporter 20 and blowing air to the smear region on slide glass 10. Drier 40 includes a fan. Drier 40 can dry the sample smeared on slide glass 10 with the air blown by the fan. Drier 40 passes slide glass 10 with the dried sample to accommodation unit 50. In the configuration example of FIG. 2, drier 40 is disposed on the Y1-direction side of sample smearing unit 33.

Accommodation unit 50 receives slide glass 10 with the dried smeared sample from drier 40 and accommodates slide glass 10. Accommodation unit 50 passes accommodated slide glass 10 to staining unit 60. Accommodation unit 50 accommodates received slide glass 10 upright in the vertical direction (Z-direction). In the configuration example of FIG. 2, accommodation unit 50 is disposed on the front side (Y1-direction side) of smear preparation apparatus 200. This can facilitate operations to be performed on accommodation unit 50. Such operations on accommodation unit 50 include, for example, operations of collecting, checking, and installing slide glass 10 with the sample smeared thereon, and the like. In the configuration example of FIG. 2, accommodation unit 50 is disposed on the Y1-direction side of drier 40.

Staining unit 60 performs staining processing on the sample on slide glass 10 finished with the smearing processing by sample smearing unit 33. Staining unit 60 performs staining processing and cleaning processing in a staining tank and a cleaning tank, respectively, for smeared slide glass 10 dried by drier 40. In the configuration example of FIG. 2, staining unit 60 is disposed on the Y2-direction side of accommodation unit 50.

Drier 70 has a function to dry slide glass 10 stained by staining unit 60. Drier 70 passes dried slide glass 10 to storage unit 80. In the configuration example of FIG. 2, drier 70 is disposed on the Y2-direction side of staining unit 60.

Storage unit 80 has a function to store stained slide glass 10.

With such a configuration, smear preparation apparatus 200 can automatically prepare smears by performing the print processing, sample smearing processing, and staining processing on slide glass 10.

(Configuration of Slide Glass Transporter)

Next, with reference to FIGS. 3 to 14, a configuration example of slide glass transporter 20 is described.

Figure 3:
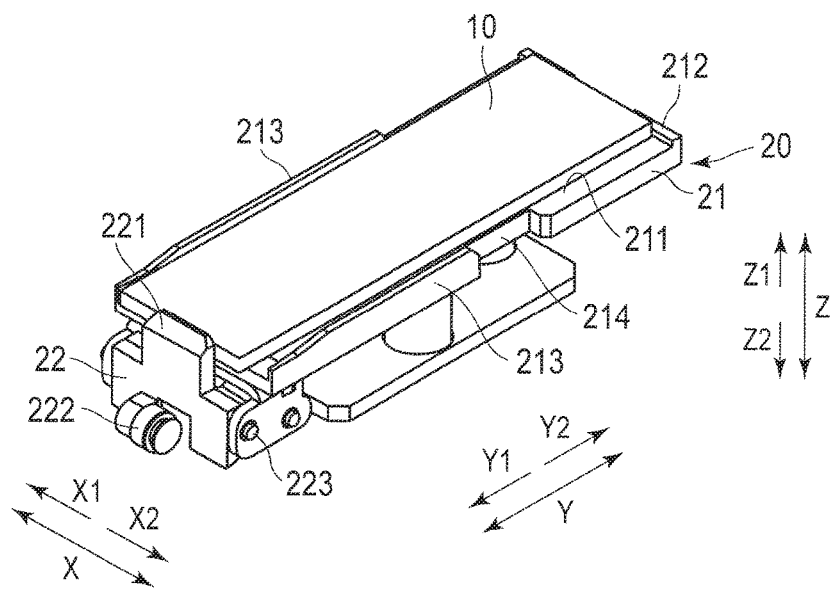
FIG. 3 is a perspective view illustrating a specific configuration example of a slide glass transporter.
Figure 4:
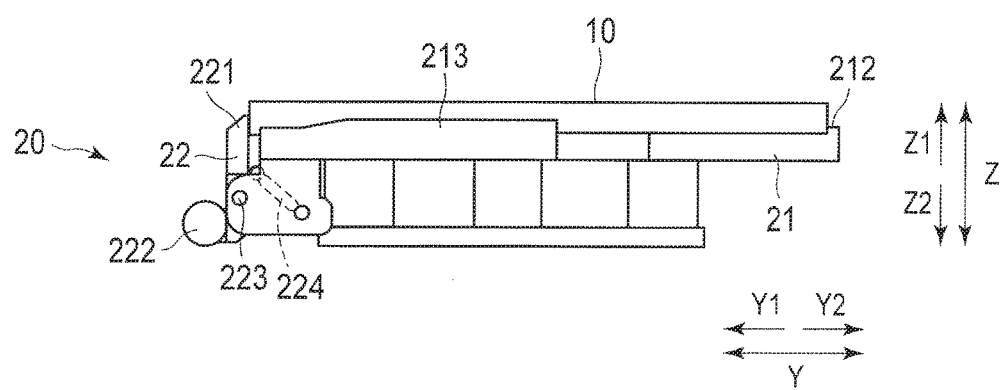
FIG. 4 is a side view illustrating a specific configuration example of the slide glass transporter.

In the configuration example illustrated in FIGS. 3 and 4, slide glass transporter 20 includes slide glass holder 21. Slide glass holder 21 includes catcher 22, mounting part 211, abutting part 212, movement regulators 213, and notch part 214. Catcher 22 includes pressure member 221, opening and closing part 222, rotary shaft 223, and spring member 224.

Slide glass holder 21 can hold slide glass 10. To be more specific, slide glass holder 21 uses mounting part 211 to support slide glass 10 from below (Z2-direction side). Moreover, slide glass holder 21 uses abutting part 212 and catcher 22 to hold slide glass 10 while sandwiching the slide glass in the longitudinal direction. Thus, slide glass holder 21 can hold slide glass 10 so that slide glass 10 does not move.

Mounting part 211 is formed to have a plate shape extending in the horizontal direction (XY direction). Abutting part 212 and movement regulators 213 are formed to protrude upward from an upper surface (Z1-direction side surface) of mounting part 211. Abutting part 212 is disposed on the Y2-direction side of slide glass holder 21. More specifically, abutting part 212 is disposed on a side in the traveling direction (Y2-direction side) to which slide glass 10 travels when slide glass holder 21 receives slide glass 10 from first slide glass feeder 11 or second slide glass feeder 12. In the configuration example illustrated in FIGS. 3 and 4, abutting part 212 is disposed in the vicinity of the Y2-direction side end of slide glass holder 21. Thus, movement of slide glass 10 in the Y2-direction is regulated by slide glass 10 coming into contact with abutting part 212.

A pair of movement regulators 213 are provided on either side of slide glass holder 21 in the X-direction. Thus, movement of slide glass 10 in the X-direction is regulated. More specifically, movement regulators 213 are provided in a pair in the X-direction perpendicular to a direction of receiving slide glass 10 from first slide glass feeder 11 or second slide glass feeder 12 by slide glass holder 21. In other words, movement regulators 213 are provided in a pair so as to face each other in the short-side direction of slide glass 10 held by slide glass holder 21. Moreover, a pair of movement regulators 213 are disposed facing each other at an interval larger than the short-side length of slide glass 10. In the configuration example illustrated in FIGS. 3 and 4, movement regulators 213 are disposed in the vicinity of the X1-direction side end of slide glass holder 21 and in the vicinity of the X2-direction side end thereof. Thus, slide glass 10 can be prevented from running off slide glass holder 21 in the X-direction.

Notch part 214 is provided on the X2-direction side of slide glass holder 21. Also, notch part 214 is formed to be shifted in the Y2-direction from the center of slide glass holder 21 in the Y-direction. Moreover, notch part 214 is formed to extend for a predetermined length in the X1-direction.

Catcher 22 is disposed on the Y1-direction slide of slide glass holder 21. More specifically, catcher 22 is disposed on the opposite side (Y1-direction side) in the traveling direction of slide glass 10 traveling when slide glass holder 21 receives slide glass 10 from first slide glass feeder 11 or second slide glass feeder 12. Moreover, catcher 22 can catch slide glass 10 while biasing (e.g., urging against, pressing against) slide glass 10 toward abutting part 212. More specifically, catcher 22 can bias slide glass 10 in the Y2-direction.

To be more specific, pressure member 221 of catcher 22 can press slide glass 10 in the Y2-direction by coming into contact with the Y1-direction side of slide glass 10. Also, catcher 22 can turn about rotary shaft 223. Moreover, catcher 22 uses spring member 224 to pull pressure member 221 in the Y2-direction. Thus, catcher 22 can bias slide glass 10 in the Y2-direction. Furthermore, catcher 22 can turn about rotary shaft 223 against the tensile force of spring member 224 by pushing opening and closing part 222 in the Y2-direction.

Pressure member 221 is disposed above (on the Z1-direction side of) rotary shaft 223. Opening and closing part 222 is disposed below (on the Z2-direction side of) rotary shaft 223. Rotary shaft 223 extends in a direction (X-direction) parallel to the short-side direction of slide glass 10 held by slide glass holder 21.

(Configuration of Transfer Mechanisms in Slide Glass Transporter)

Figure 5:
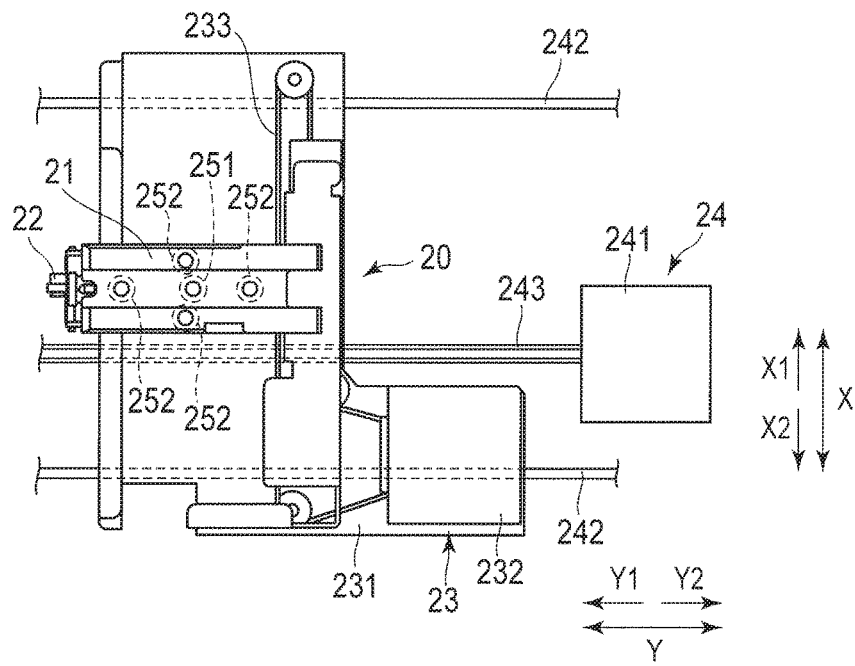
FIG. 5 is a plan view for explaining an example of a transfer mechanism in the slide glass transporter.
Figure 6:
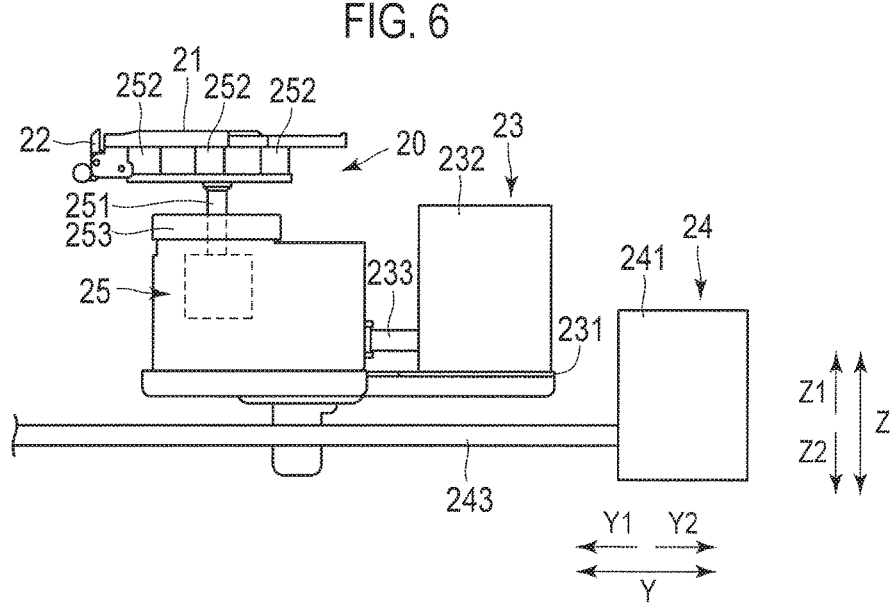
FIG. 6 is a side view for explaining an example of the transfer mechanism in the slide glass transporter.

In a configuration example illustrated in FIGS. 5 and 6, slide glass transporter 20 includes first transfer mechanism 23, second transfer mechanism 24, and third transfer mechanism 25. First transfer mechanism 23 can transfer held slide glass 10 in the X-direction that is a first direction. Second transfer mechanism 24 can transfer held slide glass 10 in the Y-direction that is a second direction. Third transfer mechanism 25 can move held slide glass 10 in the Z-direction that is the vertical direction. Thus, slide glass transporter 20 can transfer slide glass 10 within the horizontal plane and in the vertical direction. Accordingly, slide glass transporter 20 can easily transport slide glass 10 to slide processor 30 that performs processing.

First transfer mechanism 23 includes base part 231, motor 232, and belt 233. Second transfer mechanism 24 includes motor 241, a pair of rails 242, and belt 243. Third transfer mechanism 25 includes air cylinder 251, four spring members 252, and movement regulation member 253.

Motor 232 in first transfer mechanism 23 is disposed on base part 231. Slide glass holder 21 is disposed above base part 231, and can be moved in the X-direction along an unillustrated X-direction rail. To be more specific, belt 233 is rotated by driving motor 232, and thus slide glass holder 21 is moved in the X-direction. Base part 231 can be moved in the Y-direction on rail 242 in second transfer mechanism 24.

Second transfer mechanism 24 can transfer slide glass holder 21 in the Y-direction by moving base part 231 in the Y-direction. To be more specific, belt 243 is rotated by driving motor 241, and thus slide glass holder 21 is moved in the Y-direction.

Third transfer mechanism 25 is driven by air pressure, and can transfer slide glass holder 21 in the Z-direction. Air cylinder 251 can extend and contract in the vertical direction (Z-direction). Air cylinder 251 extends to move slide glass holder 21 upward (in the Z1-direction), and contracts to move slide glass holder 21 downward (in the Z2-direction). Thus, slide glass holder 21 can be moved in the vertical direction by using air pressure for aspirating the sample and air pressure for removing the extraneous matter. This eliminates the need for providing an additional motor for moving slide glass holder 21 in the vertical direction.

Spring members 252 are provided such that two thereof are disposed at a predetermined interval in the long-side direction (Y-direction) of slide glass 10 held by slide glass holder 21 and the other two thereof are disposed at a predetermined interval in the short-side direction (X-direction) thereof. More specifically, four spring members 252 are arranged at vertices of a diamond shape, respectively. Spring members 252 have a function to adjust the posture of slide glass 10 held by slide glass holder 21. Movement regulation member 253 can regulate vertical movement of slide glass holder 21 to be moved by air cylinder 251.

(Configuration of Catcher in Slide Glass Transporter)

Figure 7:
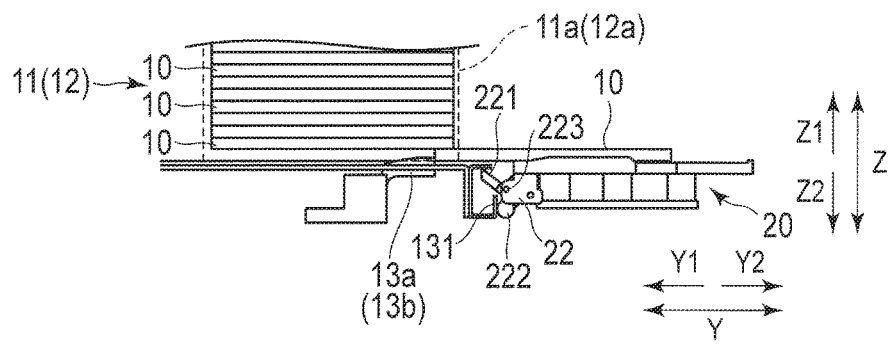
FIG. 7 is a side view for explaining a released position of a catcher in the slide glass transporter.
Figure 8:
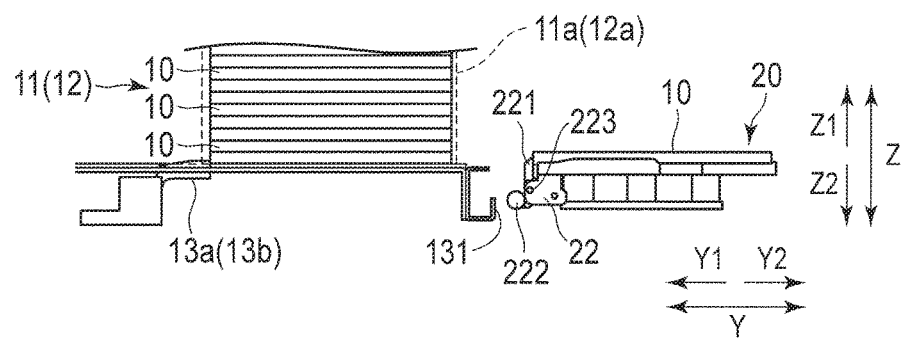
FIG. 8 is a side view for explaining a catching position of the catcher in the slide glass transporter.

With reference to FIGS. 7 and 8, description is given of a configuration of catcher 22 in slide glass transporter 20. Catcher 22 can be moved between a released position (see FIG. 7) where slide glass holder 21 passes slide glass 10 and a catching position (see FIG. 8) where slide glass holder 21 catches slide glass 10. To be more specific, catcher 22 can be moved between the released position where pressure member 221 is turned and retreated below mounting part 211 and the catching position where pressure member 221 is turned to protrude above mounting part 211. Thus, slide glass 10 can be transferred in the horizontal direction and passed from slide glass holder 21. Therefore, the apparatus configuration can be simplified compared with a case where slide glass 10 is transferred by lifting slide glass 10 in the vertical direction or the like. Note that, in the example illustrated in FIGS. 7 and 8, the description is given of the case where slide glass transporter 20 receives slide glass 10 from first slide glass feeder 11. Note that the same configuration is also adopted when slide glass transporter 20 receives slide glass 10 from second slide glass feeder 12.

First deliverer 13a for delivering slide glass 10 is provided below first slide glass feeder 11. Also, second deliverer 13b for delivering slide glass 10 is provided below second slide glass feeder 12. Moreover, contact member 131 is provided at a reception position of slide glass 10. Slide glass transporter 20 moves and brings catcher 22 into contact with contact member 131 disposed at the reception position of slide glass 10, thereby moving catcher 22 to the released position. To be more specific, slide glass holder 21 brings opening and closing part 222 of catcher 22 into contact with contact member 131 disposed below the Y2-direction side of first slide glass feeder 11, thereby pushing opening and closing part 222 in the Y2-direction. More specifically, opening and closing part 222 is pressed against contact member 131 by slide glass holder 21 moving in the Y1-direction. Thus, pressure member 221 of catcher 22 is turned about rotary shaft 223 and moved downward. As a result, the Y1-direction side of slide glass holder 21 is opened to enable horizontal transfer of slide glass 10. As described above, catcher 22 can be moved to the released position by moving slide glass holder 21 in the Y1-direction. This eliminates the need for additionally providing a dedicated drive unit for opening and closing catcher 22. As a result, the apparatus configuration can be simplified.

In a state where catcher 22 is located at the released position, first deliverer 13a pushes out slide glass 10 in the Y2-direction, thereby feeding slide glass 10 from first slide glass feeder 11 to slide glass transporter 20. More specifically, first deliverer 13a delivers a slide glass from first slide glass feeder 11 to slide glass transporter 20 located at first slide glass feeding position 111. First deliverer 13a can be moved in the Y-direction. Also, first deliverer 13a delivers lowest slide glass 10 in first slide glass feeder 11 to slide glass transporter 20. Note that, in the case of delivering slide glass 10 from second slide glass feeder 12 to slide glass transporter 20, second deliverer 13b delivers a slide glass from second slide glass feeder 12 to slide glass transporter 20 located at second slide glass feeding position 121. Second deliverer 13b can be moved in the Y-direction. Also, second deliverer 13b delivers lowest slide glass 10 in second slide glass feeder 12 to slide glass transporter 20. Thus, slide glasses 10 can be fed one by one to slide glass transporter 20 from first slide glass feeder 11 or second slide glass feeder 12.

After receiving slide glass 10 from first slide glass feeder 11 or second slide glass feeder 12, slide glass transporter 20 is moved in the Y2-direction. Thus, catcher 22 is moved to the catching position to catch slide glass 10. To be more specific, opening and closing part 222 of catcher 22 is separated from contact member 131 disposed below the Y2-direction side of first slide glass feeder 11. Thus, pressure member 221 of catcher 22 is turned about rotary shaft 223 by spring member 224, and is thus moved upward. Moreover, pressure member 221 presses slide glass 10 in the Y2-direction. As a result, slide glass 10 is held by slide glass holder 21.

(X-Direction Positioning Configuration in Slide Glass Transporter)

Figure 9:
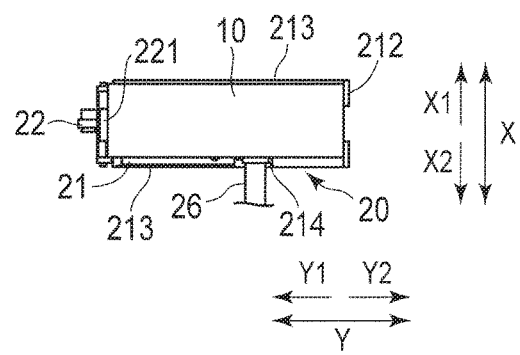
FIG. 9 is a plan view for explaining X-direction positioning of the slide glass in the slide glass transporter.

With reference to FIG. 9, description is given of an X-direction positioning configuration in slide glass transporter 20. Pusher 26 pushes slide glass 10, which is held by slide glass transporter 20, in the X1-direction, thereby bringing slide glass 10 into contact with movement regulator 213 on the X1-direction side. Thus, slide glass 10 is positioned in the X-direction relative to slide glass transporter 20. More specifically, pusher 26 can push slide glass 10, which is held by slide glass transporter 20, from one of the pair of movement regulators 213, thereby bringing slide glass 10 into contact with the other movement regulator 213. Pusher 26 includes a plunger, for example. Moreover, pusher 26 pushes slide glass 10, which is held by slide glass transporter 20, in notch part 214 provided in slide glass holder 21. Thus, pusher 26 can push slide glass 10 in the X-direction without coming into contact with movement regulator 213 on the X2-direction side. Pusher 26 is disposed at a position for the print processing by printer 32, for example.

(Vertical Transfer Configuration in Slide Glass Transporter)

Figure 10:
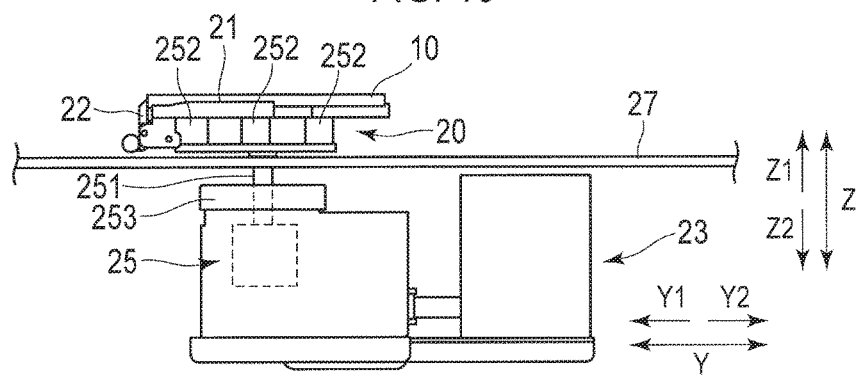
FIG. 10 is a first side view for explaining vertical transfer in the slide glass transporter.
Figure 11:
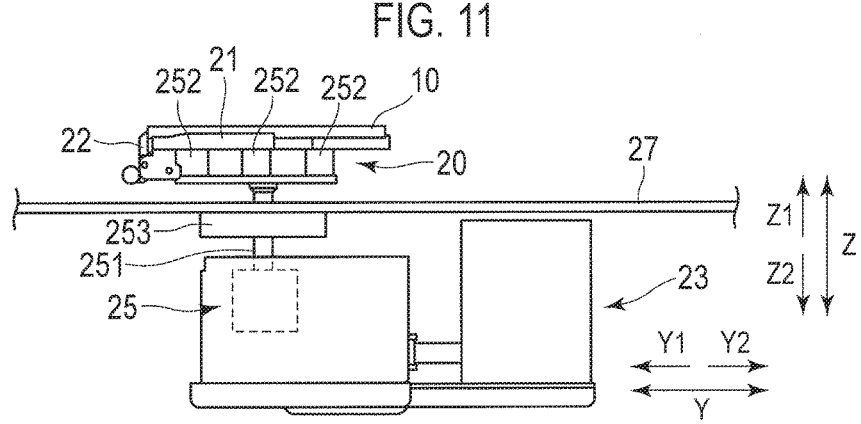
FIG. 11 is a second side view for explaining vertical transfer in the slide glass transporter.
Figure 12:
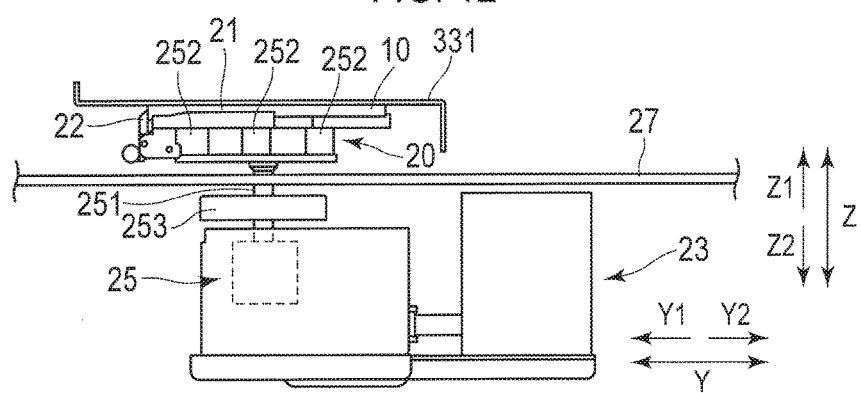
FIG. 12 is a third side view for explaining vertical transfer in the slide glass transporter.

With reference to FIGS. 10 to 12, description is given of a vertical transfer configuration in slide glass transporter 20. Slide glass holder 21 in slide glass transporter 20 is vertically moved by third transfer mechanism 25. Plate-like member 27 is provided below slide glass holder 21. A hole for inserting air cylinder 251 in third transfer mechanism 25 is formed in plate-like member 27. Plate-like member 27 is disposed between slide glass holder 21 and movement regulation member 253.

As illustrated in FIG. 10, when air cylinder 251 is lowered, slide glass holder 21 in slide glass transporter 20 is set in a lowered state. In this lowered state, slide glass 10 is fed to slide glass transporter 20 from first slide glass feeder 11 or second slide glass feeder 12. Also, in the lowered state, extraneous matter remover 31 performs extraneous matter removal processing on slide glass 10 held by slide glass holder 21. Moreover, in the lowered state, slide glass holder 21 is moved in the horizontal direction (XY-direction).

As illustrated in FIG. 11, when air cylinder 251 is lifted, a lifted position of slide glass holder 21 is determined by movement regulation member 253 coming into contact with plate-like member 27. Thus, the lifted position of slide glass holder 21 can be determined without providing a positioning member above slide glass 10. In the lifted state set by movement regulation member 253, printer 32 performs print processing on slide glass 10 held by slide glass holder 21.

As illustrated in FIG. 12, when air cylinder 251 is lifted, a lifted position of slide glass holder 21 is determined by slide glass 10 held by slide glass holder 21 coming into contact with positioning member 331 disposed above slide glass holder 21. Thus, even when there is a variation in thickness (length in the Z-direction) of slide glass 10, the upper surface of slide glass 10 can be positioned at a certain height. In the lifted state set by positioning member 331, sample smearing unit 33 performs sample smearing processing on slide glass 10 held by slide glass holder 21.

(Configuration for Passing Slide Glass among Slide Glass Transporter, Drier, and Accommodation Unit)

Figure 13:
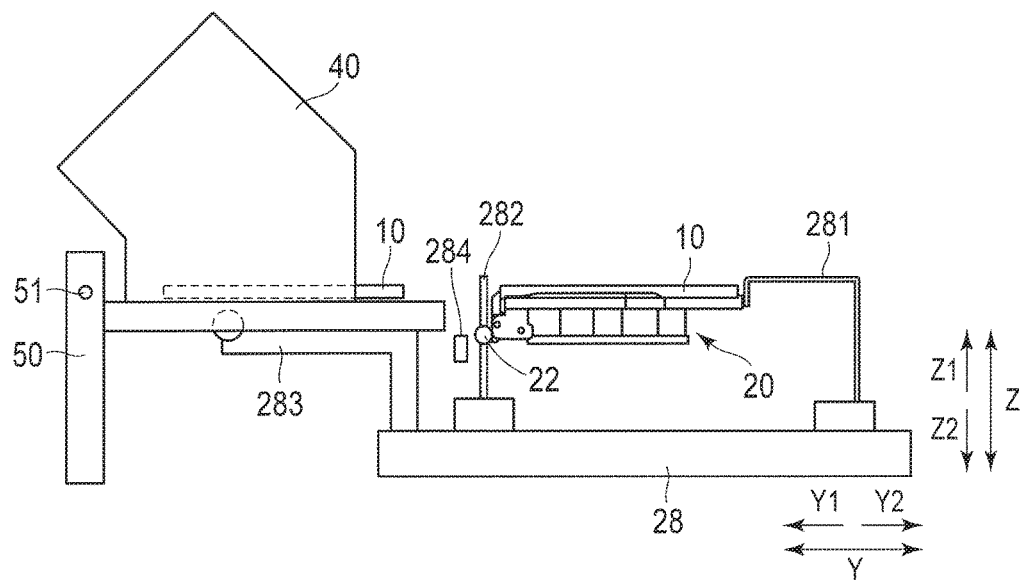
FIG. 13 is a first side view for explaining passing of slide glasses among the slide glass transporter, a drier, and an accommodation unit.
Figure 14:
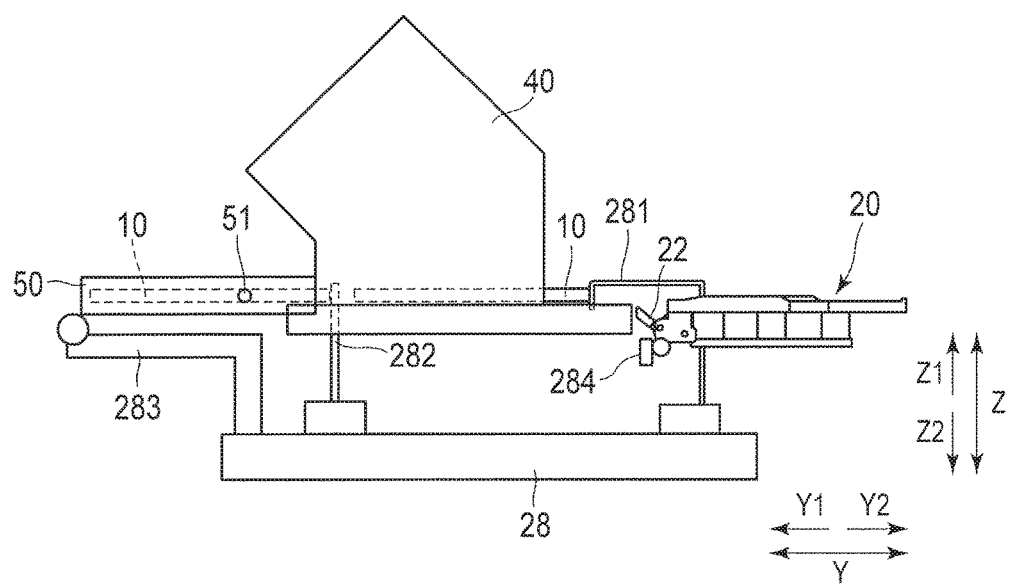
FIG. 14 is a second side view for explaining passing of slide glasses among the slide glass transporter, the drier, and the accommodation unit.

With reference to FIGS. 13 and 14, description is given of a configuration for passing slide glass 10 among slide glass transporter 20, drier 40, and accommodation unit 50. Third deliverer 28 for delivering slide glass 10 with the sample smeared thereon from slide glass transporter 20 to drier 40 is provided at a position where sample smearing unit 33 is disposed. Thus, slide glass 10 transported by slide glass transporter 20 can be easily passed to drier 40. Third deliverer 28 can pass slide glass 10 by pushing out slide glass 10 to drier 40 from slide glass transporter 20. Moreover, third deliverer 28 can also pass slide glass 10 by pushing out slide glass 10 to accommodation unit 50 from drier 40.

To be more specific, third deliverer 28 can be moved in the Y-direction. Also, third deliverer 28 delivers slide glass 10 in the opposite direction (Y1-direction) from the traveling direction of slide glass 10 when slide glass transporter 20 receives slide glass 10 from first slide glass feeder 11 or second slide glass feeder 12. Then, slide glass 10 is passed to drier 40 from slide glass transporter 20. Thus, drier 40 as well as first and second slide glass feeders 11 and 12 can be disposed on the same side (Y1-direction side) of sample smearing unit 33. As a result, smear preparation apparatus 200 can be suppressed from getting increased in size in the Y-direction, unlike a case where first and second slide glass feeders 11 and 12, sample smearing unit 33, and drier 40 are sequentially arranged in the Y2-direction.

Moreover, third deliverer 28 includes first pusher 281, second pusher 282, third pusher 283, and contact member 284. First pusher 281 can deliver slide glass 10 to drier 40 from slide glass transporter 20 positioned in sample smearing unit 33. To be more specific, first pusher 281 can push slide glass 10 in slide glass transporter 20 toward drier 40 by moving in the Y1-direction. Also, first pusher 281 returns to a position for transporting next slide glass 10 by moving in the Y2-direction. Second pusher 282 can deliver slide glass 10 in drier 40 to accommodation unit 50. To be more specific, second pusher 282 can push slide glass 10 in drier 40 toward accommodation unit 50 by moving in the Y1-direction in a lifted state. Also, second pusher 282 returns to a position for transporting next slide glass 10 by moving in the Y2-direction in a lowered state.

Third pusher 283 can turn accommodation unit 50 by pushing accommodation unit 50 in the Y1-direction. To be more specific, accommodation unit 50 can be turned about rotary shaft 51. Moreover, in the case of delivering slide glass 10 to accommodation unit 50 from drier 40, accommodation unit 50 is turned to have a posture that extends in the horizontal direction. More specifically, accommodation unit 50 is pushed by third pusher 283 to have a posture that extends in the horizontal direction. Then, after receiving slide glass 10 in the horizontal posture, accommodation unit 50 is turned to have a posture that extends in the vertical direction. More specifically, retreating of third pusher 283 in the Y2-direction allows accommodation unit 50 to have a posture that extends in the vertical direction by gravity. Thus, slide glass 10 in the horizontal posture can be set upright in the vertical posture.

First pusher 281, second pusher 282, and third pusher 283 are moved in the Y-direction in conjunction with each other. More specifically, one drive unit moves first to third pushers 281 to 283. Therefore, the operation of delivering slide glass 10 to drier 40 from slide glass transporter 20 positioned in sample smearing unit 33 and the operation of delivering slide glass 10 to accommodation unit 50 from drier 40 can be easily simultaneously performed.

Contact member 284 can move catcher 22 to the released position by coming into contact with catcher 22 in slide glass transporter 20.

(Smear Preparation Operation by Smear Preparation Apparatus)

Figure 15:
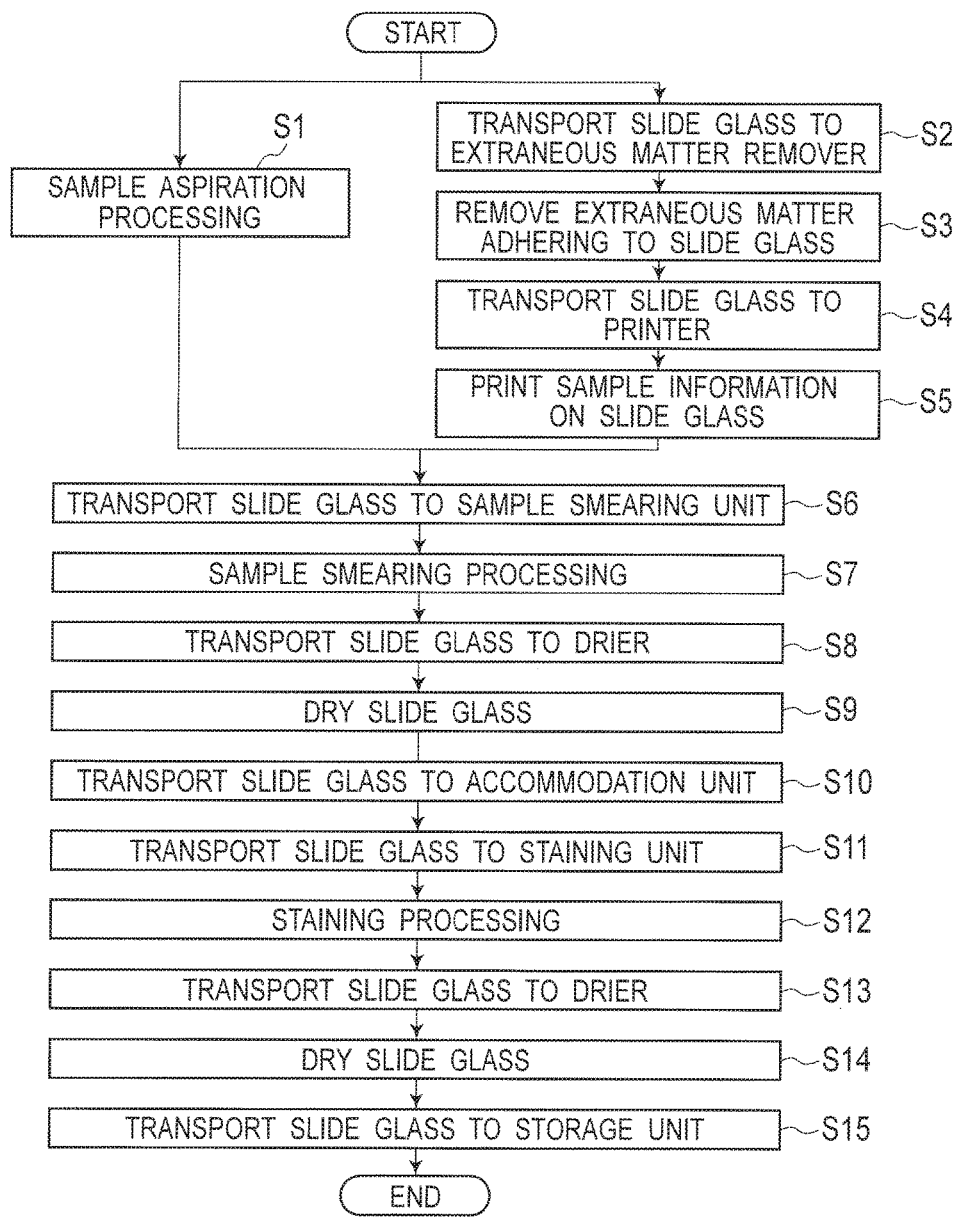
FIG. 15 is a flowchart illustrating smear preparation processing.

With reference to FIG. 15, description is given of a smear preparation operation by smear preparation apparatus 200.

First, in Step S1 of FIG. 15, sample aspiration processing is performed. More specifically, a sample for smearing processing is aspirated from a set sample container. In parallel with the processing in Step S1, slide glass 10 is transported to extraneous matter remover 31 in Step S2. To be more specific, slide glass 10 is fed to slide glass transporter 20 from first slide glass feeder 11 or second slide glass feeder 12. Then, slide glass 10 held by slide glass transporter 20 is transported to extraneous matter remover 31. In Step S3, extraneous matter remover 31 performs extraneous matter removal processing on slide glass 10 held by slide glass transporter 20.

In Step S4, slide glass 10 is transported to printer 32. To be more specific, slide glass 10 held by slide glass transporter 20 is transported to printer 32. In Step S5, printer 32 performs printing of sample information on slide glass 10 held by slide glass transporter 20.

In Step S6, slide glass 10 is transported to sample smearing unit 33. To be more specific, slide glass 10 held by slide glass transporter 20 is transported to sample smearing unit 33. In Step S7, sample smearing unit 33 performs sample smearing processing on slide glass 10 held by slide glass transporter 20.

In Step S8, slide glass 10 is transported to drier 40. To be more specific, third deliverer 28 passes slide glass 10 to drier 40 from slide glass transporter 20. In Step S9, drier 40 performs drying processing on the sample smeared on slide glass 10.

In Step S10, slide glass 10 is transported to accommodation unit 50. To be more specific, third deliverer 28 passes slide glass 10 to accommodation unit 50 from drier 40. In Step S11, slide glass 10 is transported to staining unit 60. To be more specific, slide glass 10 is passed to staining unit 60 from accommodation unit 50. In Step S12, staining unit 60 performs staining processing on the sample smeared on slide glass 10.

In Step S13, slide glass 10 is transported to drier 70. To be more specific, slide glass 10 is passed to drier 70 from staining unit 60. In Step S14, drier 70 performs drying processing on the sample smeared and stained on slide glass 10. Thus, a smear is prepared on slide glass 10.

In Step S15, slide glass 10 is transported to storage unit 80. To be more specific, slide glass 10 is passed to storage unit 80 from drier 70. Then, slide glass 10 with the smear prepared thereon is stored in storage unit 80. Then, the smear preparation processing is terminated.

[Overview of Deliverer]

With reference to FIGS. 16 to 19, description is given of an overview of a deliverer in the sample smearing apparatus according to this embodiment.

Deliverer 13 can deliver slide glass 10 to the slide glass transporter from the slide glass feeder.

Figure 16:
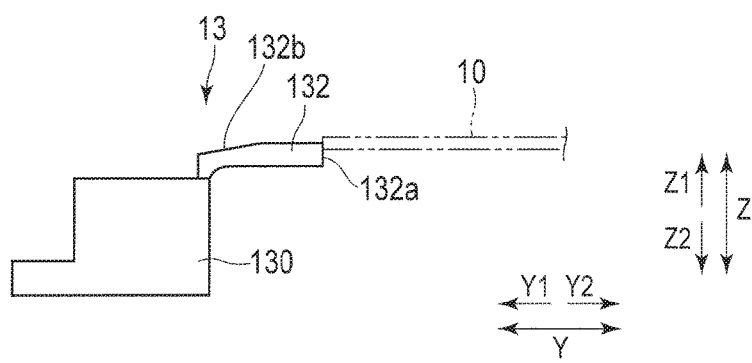
FIG. 16 is a side view illustrating an overview of a deliverer.

As illustrated in FIG. 16, deliverer 13 includes pusher member 130. Pusher member 130 includes pushing contact part 132a and inclined part 132b. The slide glass feeder includes a supporter that supports slide glass 10, and holds slide glasses 10 stacked upward on the supporter. Pusher member 130 protrudes upward (in the Z1-direction) with respect to the lower end of slide glass 10 supported by the supporter in the slide glass feeder. In other words, pusher member 130 protrudes upward with respect to the lower surface (surface in the Z2-direction) of lowest slide glass 10 among stacked slide glasses 10. Moreover, pusher member 130 can push slide glass 10 in a predetermined direction (Y2-direction). Pushing contact part 132a is disposed on one side in the predetermined direction (Y2-direction side) of pusher member 130. Also, pushing contact part 132a comes into contact with slide glass 10 during delivering of slide glass 10. Inclined part 132b is disposed at the upper end of pusher member 130 on the opposite side (Y1-direction side) in the predetermined direction. Moreover, inclined part 132b is inclined downward while extending in the opposite direction (toward Y1-direction side) from the predetermined direction.

Figure 17:
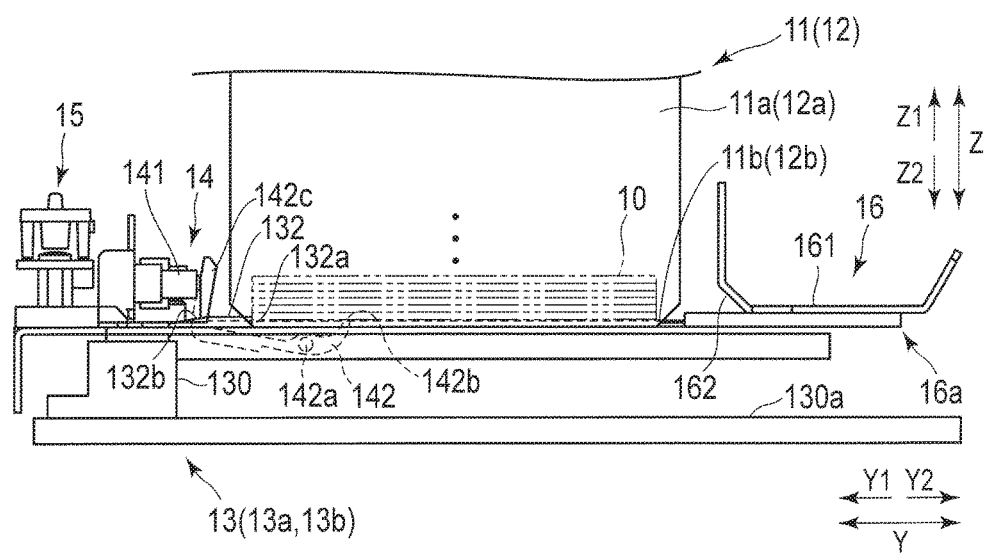
FIG. 17 is a side view illustrating an overview of a periphery including the deliverer.

To be more specific, as illustrated in FIG. 17, deliverer 13 includes first deliverer 13a and second deliverer 13b. First deliverer 13a can deliver slide glass 10 to slide glass transporter 20 located at first slide glass feeding position 111 from first slide glass feeder 11. Second deliverer 13b can deliver slide glass 10 to slide glass transporter 20 located at second slide glass feeding position 121 from second slide glass feeder 12. More specifically, deliverer 13 delivers slide glasses 10 from the slide glass feeders. Note that first deliverer 13a and second deliverer 13b have the same configuration. Deliverer 13 includes pusher member 130 and drive unit 130a. Pusher member 130 includes claw part 132. Claw part 132 includes pushing contact part 132a and inclined part 132b.

Pusher member 130 protrudes upward (in the Z1-direction) from the lower end of slide glass 10 supported by supporter 11b in first slide glass feeder 11 or supporter 12b in second slide glass feeder 12. In other words, pusher member 130 protrudes upward (in the Z1-direction) from the lower surface of lowest slide glass 10 among slide glasses 10 stacked in first slide glass feeder 11 or second slide glass feeder 12. Note that supporter 11b is provided in first slide glass feeder 11, and supports slide glasses 10 from below. Likewise, supporter 12b is provided in second slide glass feeder 12, and supports slide glasses 10 from below. Pusher member 130 can push slide glass 10 in a third direction (Y2-direction (predetermined direction)). Supporter 11b in first slide glass feeder 11 and supporter 12b in second slide glass feeder 12 are formed to extend in the Y-direction. Supporters 11b and 12b may be formed in a flat plate shape or a rail shape as long as supporters 11b and 12b can support slide glasses 10 from below. First slide glass feeder 11 uses first case part 11a to hold slide glasses 10. Second slide glass feeder 12 uses second case part 12a to hold slide glasses 10. Note that second slide glass feeder 12 may include no second case part 12a.

Drive unit 130a can move pusher member 130 back and forth in a direction (Y-direction) parallel to the third direction. For example, drive unit 130a includes a motor, a belt, and a pulley, and may use a belt pulley mechanism to move pusher member 130 in the direction parallel to the third direction. Alternatively, drive unit 130a may use a linear motor mechanism to move pusher member 130 in the direction parallel to the third direction.

A pair of claw parts 132 are provided for one pusher member 130. The pair of claw parts 132 are arranged in parallel along a direction (X-direction) perpendicular to the third direction in the horizontal direction. Note that the pair of claw parts 132 have the same configuration. Alternatively, one claw part 132 or three or more claw parts 132 may be provided for one pusher member 130. Each claw part 132 has pushing contact part 132a provided at its end (Y2-direction side end) in the third direction. Claw part 132 also has inclined part 132b provided on the opposite side (Y1-direction side) in the third direction. Claw part 132 protrudes upward (in the Z1-direction) by predetermined distance L1 (see FIG. 19) from the lower end of slide glass 10 supported by supporter 11b or 12b. For example, pushing contact part 132a of claw part 132 protrudes upward by a distance smaller than the thickness of slide glass 10 with respect to the lower end of slide glass 10 supported by supporter 11b or 12b. It is preferable that pushing contact part 132a of claw part 132 protrudes upward by a distance ⅓ or more of the thickness of slide glass 10 with respect to the lower end of slide glass 10 supported by supporter 11b or 12b. It is more preferable that pushing contact part 132a of claw part 132 protrudes upward by a distance ½ or more of the thickness of slide glass 10 with respect to the lower end of slide glass 10 supported by supporter 11b or 12b.

Inclined part 132b of claw part 132 is inclined downward (in the Z2-direction) in the opposite direction (Y1-direction) from the third direction. More specifically, inclined part 132b is inclined downward in the opposite direction (Y1-direction) from a direction of delivering slide glass 10. Inclined part 132b is inclined between the upper end of claw part 132 and at least the lower surface of lowest slide glass 10 among stacked slide glasses 10. It is preferable that inclined part 132b is inclined between the upper end of claw part 132 and a position below the lower surface of lowest slide glass 10 among stacked slide glasses 10. More specifically, when pusher member 130 is moved in the Y1-direction, slide glass 10 runs on inclined part 132b, and is moved upward for protrusion from the lower end of slide glass 10 supported by supporter 11b or 12b in pusher member 130.

With the above configuration, pushing contact part 132a comes into contact with the end face of slide glass 10 by moving pusher member 130 in deliverer 13 in the third direction (Y2-direction). Thus, slide glass 10 can be delivered. Moreover, slide glass 10 can be allowed to run on inclined part 132b by moving pusher member 130 in deliverer 13 in the opposite direction (Y1-direction) from the third direction. Therefore, pusher member 130 does not need to be retreated downward when returning pusher member 130. This eliminates the need for providing a mechanism for vertically moving pusher member 130. As a result, the apparatus configuration can be simplified, and thus sample smearing apparatus 100 can be reduced in size.

As illustrated in FIG. 17, first slide glass feeder 11 and second slide glass feeder 12 are configured such that slide glasses 10 can be disposed to have the longitudinal direction in a direction (Y-direction) parallel to the third direction. Moreover, pusher member 130 can sequentially deliver slide glasses 10 by moving back and forth in the direction (Y-direction) parallel to the third direction. More specifically, in the example illustrated in FIG. 17, no mechanism for vertically moving pusher member 130 is provided. Thus, the apparatus configuration can be simplified.

Furthermore, sample smearing apparatus 100 is provided with slide glass detector 14 that detects whether or not slide glasses 10 are held in first slide glass feeder 11 and second slide glass feeder 12. Thus, it can be easily determined whether or not slide glasses 10 are housed in first and second slide glass feeders 11 and 12. Therefore, when no slide glasses 10 are housed therein, replenishment of slide glasses 10 can be encouraged or the sample smearing processing can be suspended.

Slide glass detector 14 includes sensor 141 and detection lever 142. Sensor 141 includes, for example, an optical sensor that detects transmission/shielding of light. Detection lever 142 includes rotary shaft 142a, slide glass abutting part 142b, and shielding part 142c. Moreover, detection lever 142 is turned to change a light detection state of sensor 141 depending on the presence or absence of slide glass 10. Sensor 141 is disposed in the Y1-direction with respect to first case part 11a or second case part 12a. Therefore, since sensor 141 is not disposed below slide glass 10, glass powder or the like adhering to slide glass 10 can be suppressed from dropping onto and adhering to sensor 141. As a result, erroneous detection by sensor 141 can be suppressed.

When slide glasses 10 are held in first slide glass feeder 11 or second slide glass feeder 12 based on the detection result obtained by slide glass detector 14, deliverer 13 delivers slide glasses 10 one by one from first slide glass feeder 11 or second slide glass feeder 12. Thus, when no slide glasses 10 are held in first slide glass feeder 11 or second slide glass feeder 12, driving of deliverer 13 can be suppressed. Moreover, when slide glasses 10 are held in first slide glass feeder 11 or second slide glass feeder 12 based on the detection result obtained by slide glass detector 14, the sample is aspirated by a sample aspiration mechanism in parallel with delivering of slide glasses 10. More specifically, when no slide glasses 10 are housed in first slide glass feeder 11 or second slide glass feeder 12, the sample is not aspirated.

Furthermore, sample smearing apparatus 100 is provided with display unit 15 that displays states based on the detection result obtained by slide glass detector 14. Display unit 15 uses light, for example, to display the states. Display unit 15 may include LED elements. Display unit 15 displays in a differentiable manner a state where slide glasses 10 are housed in first slide glass feeder 11 or second slide glass feeder 12, a state where no slide glasses 10 are housed in first slide glass feeder 11 or second slide glass feeder 12, and a state where slide glasses 10 are housed in first slide glass feeder 11 or second slide glass feeder 12 and slide glasses 10 are sequentially delivered. For example, display unit 15 displays the states while changing colors of the light and states such as lighting and flashing, depending on the state.

Figure 18:
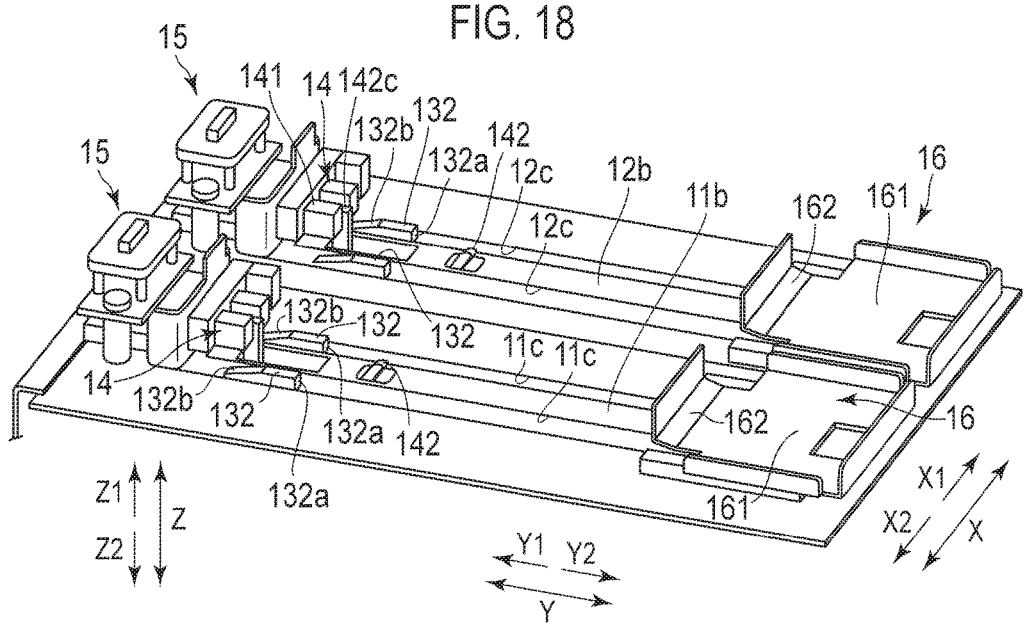
FIG. 18 is a perspective view illustrating the overview of the deliverer.

As illustrated in FIG. 18, supporter 11b in first slide glass feeder 11 and supporter 12b in second slide glass feeder 12 have elongated openings 11c and 12c provided therein, respectively, for inserting the pair of claw parts 132 in pusher member 130. Openings 11c and 12c are each provided in a pair corresponding to the number of claw parts 132. More specifically, claw parts 132 protrude upward from the lower surface of lowest slide glass 10 among stacked slide glasses 10. Moreover, supporter 11b is disposed between the pair of openings 11c and supporter 12b is disposed between the pair of openings 12c. Thus, X-direction widths of openings 11c and 12c can be suppressed from getting increased. As a result, slide glass 10 can be prevented from dropping by entering through openings 11c or 12c.

Moreover, sample smearing apparatus 100 is provided with guide member 16 that is disposed on the third direction side (Y2-direction side) of first slide glass feeder 11 and second slide glass feeder 12, and covers above (Z1-direction) slide glass 10 to be delivered. Guide member 16 includes horizontal part 161 and inclined part 162. Here, slide glass transporter 20 receives slide glass 10 from first slide glass feeder 11 or second slide glass feeder 12 at a position lower than supporter 11b or 12b so that slide glass 10 can be easily received. Guide member 16 suppresses the Y1-direction side end from being lifted by the Y2-direction side end of slide glass 10 being lowered when slide glass 10 is passed to slide glass transporter 20. Therefore, pushing contact part 132a of pusher member 130 can be suppressed from separating from slide glass 10 during delivering of slide glass 10. Thus, slide glass 10 can be surely delivered. Horizontal part 161 suppresses lifting of slide glass 10 during delivering thereof. Inclined part 162 guides slide glass 10 to space 16a (see FIG. 17) between guide member 16 and supporter 11b or 12b during delivering of slide glass 10. Inclined part 162 is inclined upward along the Y1-direction.

Figure 19:
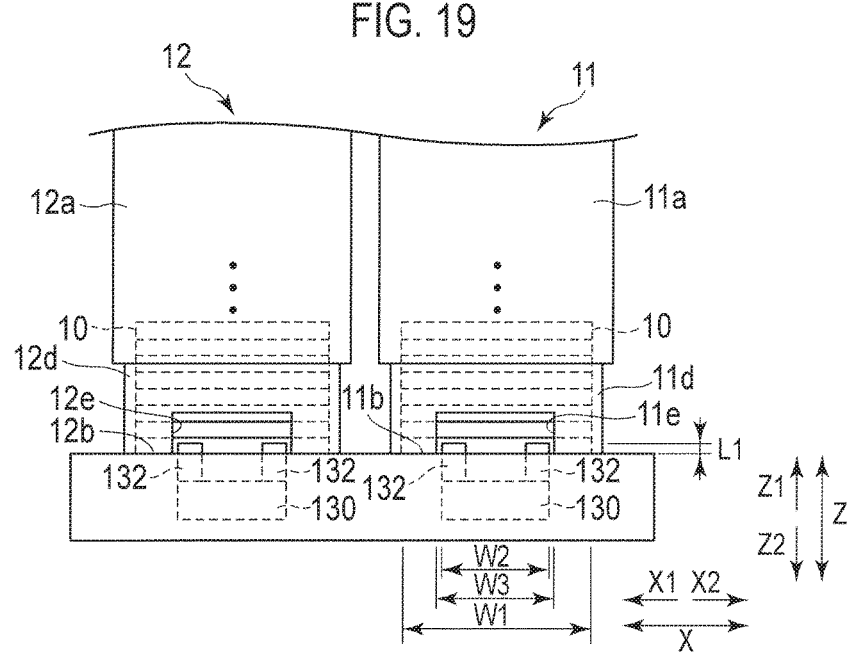
FIG. 19 is a front view illustrating the deliverer and the slide glass feeder.

As illustrated in FIG. 19, first slide glass feeder 11 includes wall part 11d vertically extending on the opposite side (Y1-direction side) in the third direction. Second slide glass feeder 12 includes wall part 12d vertically extending on the opposite side (Y1-direction side) in the third direction. In lower portions of wall parts 11d and 12d, notches 11e and 12e are provided, respectively, each having width W3 smaller than width W1 of slide glass 10 and larger than width W2 of pusher member 130 in the horizontal direction. Thus, when pusher member 130 is returned in the Y1-direction, slide glass 10 comes into contact with wall part 11d or 12d, thereby regulating movement thereof in the Y1-direction. Therefore, slide glass 10 can be lifted up along inclined part 132b of pusher member 130. In other words, pusher member 130 can be inserted below slide glass 130. Moreover, since width W2 of pusher member 130 can be increased in the horizontal direction, slide glass 10 can be surely pushed with good balance.

Moreover, pusher member 130 protrudes upward by predetermined distance L1 from the lower surface of lowest slide glass 10 among slide glasses 10 stacked in first slide glass feeder 11 and second slide glass feeder 12. For example, pusher member 130 protrudes upward by 0.5 mm to 0.8 mm from the lower surface of lowest slide glass 10 among stacked slide glasses 10. Slide glass 10 has a thickness of about 1 mm. By allowing pusher member 130 to protrude upward by 0.8 mm or less, extrusion of two slide glasses 10 at a time can be suppressed. By allowing pusher member 130 to protrude upward by 0.5 mm or more, one slide glass 10 can be surely pushed.

(Deliver Operation by Deliverer)

Figure 20:
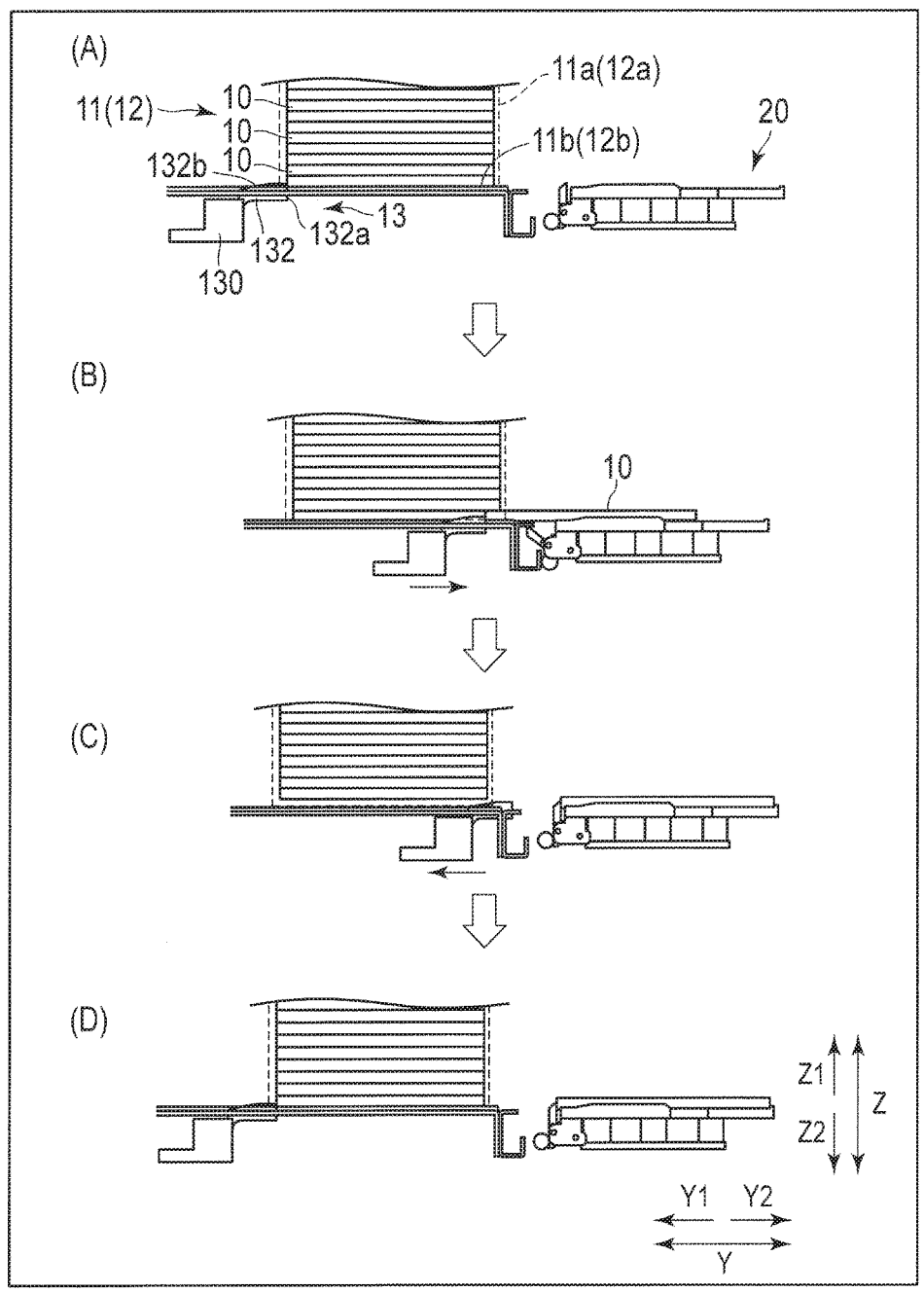
FIG. 20 is a side view for explaining a deliver operation by the deliverer.

With reference to FIG. 20, a deliver operation by deliverer 13 is described.

As illustrated in (A) of FIG. 20, pushing contact part 132a of pusher member 130 comes into contact with the Y1-direction side end face of lowest slide glass 10 in first slide glass feeder 11 or second slide glass feeder 12. Then, as illustrated in (B) of FIG. 20, lowest slide glass 10 in first slide glass feeder 11 or second slide glass feeder 12 is delivered toward slide glass transporter 20 by moving pusher member 130 in the Y2-direction.

As illustrated in (C) of FIG. 20, pusher member 130 is returned in the Y1-direction after slide glass 10 is transported to slide glass transporter 20. In this event, pusher member 130 is moved in the Y1-direction while inclined part 132b of pusher member 130 comes into contact with lowest slide glass 10 in first slide glass feeder 11 or second slide glass feeder 12 and pushes up slide glass 10.

As illustrated in (D) of FIG. 20, when pusher member 130 is moved to the Y1-direction side of slide glass 10 in first slide glass feeder 11 or second slide glass feeder 12, slide glass 10 that has been pushed up is lowered. This sets next slide glass 10 to be ready for delivery. Slide glasses 10 are sequentially delivered by repeating the operations illustrated in (A) to (D) of FIG. 20.

(Detection Operation by Slide Glass Detector)

Figure 21:
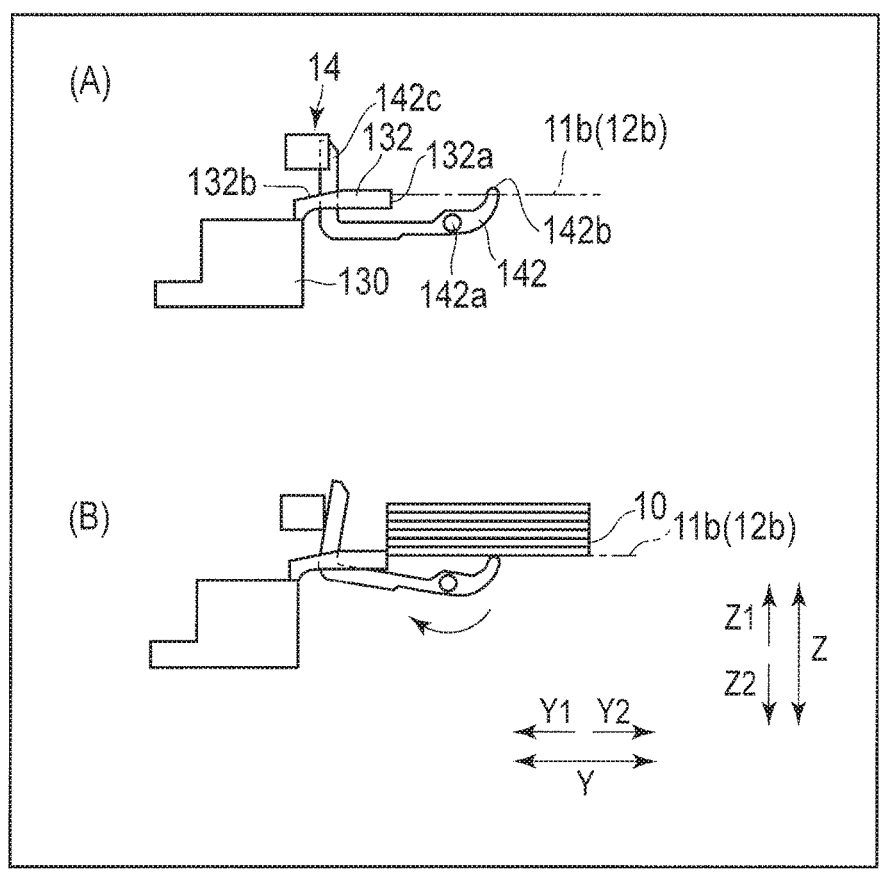
FIG. 21 is a side view for explaining a detection operation by a slide glass detector.

With reference to FIG. 21, description is given of an operation of detecting slide glass 10 by slide glass detector 14.

As illustrated in (A) of FIG. 21, when there is no slide glass 10, detection lever 142 in slide glass detector 14 has slide glass abutting part 142b not pushed by slide glass 10. Thus, shielding part 142c shields light from sensor 141. When sensor 141 detects no light, slide glass detector 14 detects that there is no slide glass 10.

As illustrated in (B) of FIG. 21, when there is slide glass 10, detection lever 142 in slide glass detector 14 has slide glass abutting part 142b pushed by slide glass 10. Thus, detection lever 142 is turned, and shielding part 142c does not shield light from sensor 141. When sensor 141 detects light, slide glass detector 14 detects that there is slide glass 10. As described above, mechanical detection is performed to detect slide glass by pushing detection lever 142 with slide glass 10. Thus, slide glass 10 can be surely detected.

(Slide Glass Feed State Display Processing)

With reference to FIG. 22, description is given of slide glass feed state display processing by sample smearing apparatus 100.

In Step S21 of FIG. 22, slide glass detector 14 acquires a storage detection result on slide glass 10. In Step S22, it is determined whether or not storage of slide glass 10 is detected. The processing advances to Step S23 if the storage is detected, and advances to Step S26 if the storage is not detected.

In Step S23, it is determined whether or not sample smearing apparatus 100 is in operation. To be more specific, it is determined whether or not slide glasses 10 are sequentially delivered from first slide glass feeder 11 or second slide glass feeder 12. The processing advances to Step S25 if sample smearing apparatus 100 is in operation, and advances to Step S24 if sample smearing apparatus 100 is not in operation.

In Step S24, green light is lighted and displayed on display unit 15. More specifically, a standby state is notified, indicating that slide glasses 10 are stored in first slide glass feeder 11 or second slide glass feeder 12 and the sample smearing processing can be performed. Then, the slide glass feed state display processing is terminated.

In Step S25, flashing yellow light is displayed on display unit 15. More specifically, a state is notified, indicating that slide glasses 10 are stored in first slide glass feeder 11 or second slide glass feeder 12 and the sample smearing processing is in execution. Then, the slide glass feed state display processing is terminated.

In Step S26, red light is lighted and displayed on display unit 15. More specifically, a state is notified, indicating that no slide glasses 10 are stored in first slide glass feeder 11 or second slide glass feeder 12 and the sample smearing processing cannot be performed. Then, the slide glass feed state display processing is terminated.

Note that the embodiment disclosed herein is to be considered in all respects as illustrative and not restrictive. The scope of the invention is indicated by the appended claims, rather than by the foregoing description of the embodiment, and all changes (modified examples) which come within the meaning and range of equivalency of the claims are therefore intended to be embraced therein.

For example, as in a modified example illustrated in FIG. 23, a deliver direction rear end (Y1-direction end) of a pressure member in a deliverer may be formed to be long, and slide glass 10 may be pushed to a slide glass feeding position while supporting next slide glass 10 on an upper surface of the pressure member. Therefore, next slide glass 10 is not lowered below the pressure member. Thus, the pressure member can be easily slid under slide glass 10 and returned.

Moreover, a jack mechanism may be provided, which supports a next slide glass from below when the pressure member in the deliverer pushes a slide glass. Therefore, the next slide glass is supported by the jack mechanism. Thus, the pressure member can be easily slid under slide glass 10 and returned.

One or more embodiments may be specified in the following paragraphs.

A sample smearing apparatus comprising:
a slide glass feeder that holds slide glasses in a stacked state; and
a deliverer that delivers the slide glasses from the slide glass feeder, wherein
the deliverer includes a pusher member that protrudes upward from a lower surface of the lowest slide glass among the stacked slide glasses, and pushes the slide glass in a predetermined direction, and
the pusher member includes a pushing contact part that is provided on one side of the pusher member in the predetermined direction and that comes into contact with the slide glass, and an inclined part that is provided at an upper end on the opposite side of the pusher member in the predetermined direction, and which is inclined downward while extending in the opposite direction from the predetermined direction.

The sample smearing apparatus may further comprises a sample smearing unit which smears a sample on the delivered slide glass.

The inclined part may be inclined from the upper end of the pusher member to a position lower than the lower surface of the lowest slide glass among the stacked slide glasses.

The slide glass feeder may be configured such that the slide glasses are locatable to have a longitudinal direction in the predetermined direction, and
the pusher member may be configured to sequentially deliver the slide glasses by moving back and forth in a direction parallel to the predetermined direction.

The sample smearing apparatus may further comprises a slide glass detector which detects if a slide glass is held in the slide glass feeder.

The deliverer may be configured to deliver slide glasses in the slide glass feeder one by one when the slide glasses are held in the slide glass feeder based on a detection result obtained by the slide glass detector.

The sample smearing apparatus may further comprises a display unit which displays states based on the detection result obtained by the slide glass detector, wherein
the display unit may display in a differentiable manner a state where the slide glasses are held in the slide glass feeder, a state where no slide glasses are held in the slide glass feeder, and a state where the slide glasses are held in the slide glass feeder and the slide glasses are sequentially delivered.

The slide glass feeder may include a wall part vertically extending on a side of the slide glass feeder in the opposite direction from the predetermined direction, and
a notch may be provided in a lower portion of the wall part, the notch having a width smaller than a width of the slide glass and larger than a width of the pushing contact part in a horizontal direction.

The pusher member may include claw parts arranged side by side along a horizontal direction perpendicular to the predetermined direction,
the pushing contact part may be provided at each of ends of the claw parts in the predetermined direction, and
elongated openings for inserting the claw parts in the pusher member may be provided in the supporter in the slide glass feeder.

The sample smearing apparatus may further comprises a guide member which is provided on one side in the predetermined direction of the slide glass feeder, and covers above the slide glass to be delivered.

The pusher member may protrude upward by 0.5 mm to 0.8 mm from the lower surface of the lowest slide glass among the slide glasses stacked in the slide glass feeder.

The embodiments of sample smearing apparatus described above reduce the sample smearing apparatus in size by simplifying the apparatus configuration.

The invention claimed is:

1. A sample smearing apparatus comprising:
   a first slide glass feeder that feeds a first slide glass among one or more first slide glasses held in the first slide glass feeder before processing;
   a slide glass transporter onto which the first slide glass at a first slide glass feeding position is fed from the first slide glass feeder, the slide glass transporter comprising: a slide glass holder that holds the first slide glass; and a transport mechanism that transports the slide glass holder; and
   a slide processor that performs processing on the first slide glass held by the slide glass holder, wherein
   the transport mechanism that transports, between the first slide glass feeding position and the slide processor, the slide glass holder.

2. The sample smearing apparatus according to claim 1, wherein
   the slide processor includes a sample smearing unit which smears a sample on the first slide glass,
   the slide glass transporter transports the held first slide glass to the sample smearing unit, and
   the sample smearing unit performs sample smearing processing on the first slide glass held by the slide glass holder.

3. The sample smearing apparatus according to one of claim 1, wherein
   the slide processor includes a printer that prints information on the first slide glass held by the slide glass holder, the slide glass transporter transports the held first slide glass to the printer, and the printer performs print processing on the first slide glass held by the slide glass holder.

4. The sample smearing apparatus according to claim 3, wherein the slide processor further includes an extraneous matter remover that removes extraneous matter adhering to the first slide glass, and the slide glass transporter transports the held first slide glass to the extraneous matter remover, and transports the first slide glass to the printer after the extraneous matter remover removes the extraneous matter so that the printer preforms printing on the first slide glass.

5. The sample smearing apparatus according to claim 1, further comprising:

a second slide glass feeder which feeds a second slide glass before processing, wherein the slide glass transporter receives the first slide glass at the first slide glass feeding position from the first slide glass feeder, receives the second slide glass at a second slide glass feeding position different from the first slide glass feeding position from the second slide glass feeder, and transports each of the received first slide glass and the second slide glass one by one while holding the first slide glass and the second slide glass with the slide glass holder.

6. The sample smearing apparatus according to claim 5, wherein the first slide glass feeder and the second slide glass feeder are arranged side by side in a short-side direction of a slide glass, the first slide glass feeding position is positioned on one side of the first slide glass feeder in a long-side direction of the slide glass, and the second slide glass feeding position is positioned on one side of the second slide glass feeder in the long-side direction of the slide glass.

7. The sample smearing apparatus according to claim 5, further comprising:

a first deliverer that delivers the first slide glass from the first slide glass feeder to the slide glass transporter located at the first slide glass feeding position; and a second deliverer that delivers the second slide glass from the second slide glass feeder to the slide glass transporter located at the second slide glass feeding position.

8. The sample smearing apparatus according to claim 5, wherein the first slide glass feeder includes a first case part that holds two or more of the first slide glass before processing in a stacked state, and the second slide glass feeder includes a second case part that holds two or more of the second slide glass before processing in a stacked state.

9. The sample smearing apparatus according to claim 1, wherein the transport mechanism of the slide glass transporter comprises:

a first transfer mechanism that transfers the held first slide glass in a first direction within a horizontal plane; and a second transfer mechanism that transfers the held first slide glass within the horizontal plane in a second direction that intersects with the first direction.

10. The sample smearing apparatus according to claim 1, further comprising:

a first deliverer that delivers the first slide glass from the first slide glass feeder to the slide glass transporter located at the first slide glass feeding position, wherein the first slide glass feeder holds two or more of the first slide glass in a vertically stacked state, the first deliverer comprises a pusher member that protrudes upward from a lower surface of the lowest first slide glass among the stacked first slide glasses, and pushes the lowest first slide glass in a third direction, wherein the pusher member comprises:

a pushing contact part in contact with the lowest first slide glass, the pushing contact part is positioned on one side of the pusher member in the third direction, and an inclined part positioned at an upper end on the opposite side of the pusher member in the third direction, the inclined part is inclined downward while extending in the opposite direction from the third direction.

11. The sample smearing apparatus according to claim 1, wherein the transport mechanism of the slide glass transporter includes a third transfer mechanism that vertically moves the held first slide glass.

12. The sample smearing apparatus according to claim 11, wherein the third transfer mechanism is driven by air pressure.

13. The sample smearing apparatus according to claim 1, wherein the slide processor includes a sample smearing unit which smears a sample on the first slide glass, the sample smearing apparatus further comprises:

a drier that dries the first slide glass with the sample smeared thereon by the sample smearing unit; and a third deliverer that delivers the first slide glass with the sample smeared thereon from the slide glass transporter to the drier.

14. The sample smearing apparatus according to claim 13, wherein the third deliverer passes the first slide glass to the drier from the slide glass transporter by delivering the first slide glass in a direction opposite from a traveling direction of the first slide glass traveling when the slide glass transporter receives the first slide glass from the first slide glass feeder.

15. The sample smearing apparatus according to claim 1, wherein the slide glass holder in the slide glass transporter comprises:

a mounting part, on an upper surface of which the first slide glass is mounted, and a catcher including a pressure member in contact with the first slide glass mounted on the mounting part and pushes an end face of the first slide glass.

16. The sample smearing apparatus according to claim 15, wherein the catcher moves between a released position where the pressure member is turned to be retreated below the mounting part and a catching position where the pressure member is turned to protrude above the mounting part.

17. The sample smearing apparatus according to claim 16, wherein the slide glass transporter moves the catcher to the released position by moving and bringing the catcher into contact with a contact member disposed at a slide glass reception position.

18. The sample smearing apparatus according to claim 15, wherein
the slide glass holder further includes movement regulators that regulate movement of the first slide glass, and
the movement regulators are provided in a pair arranged side by side in a direction perpendicular to a direction in which the first slide glass is received from the first slide glass feeder.

19. The sample smearing apparatus according to claim 18, further comprising:
a pusher that pushes the first slide glass held in the slide glass transporter from one of the pair of movement regulators, thereby bringing the first slide glass into contact with the other movement regulator.

20. The sample smearing apparatus according to claim 15, wherein
the slide glass holder further includes an abutting part positioned on one side in a traveling direction in which the first slide glass travels in a process of receiving the first slide glass from the first slide glass feeder, and in contact with the received first slide glass, and
the catcher is disposed on the opposite side in the traveling direction in the process of receiving the first slide glass, and catches the first slide glass while biasing the first slide glass toward the abutting part.

\* \* \* \* \*